US 12,213,888 B2

United States Patent
Cook et al.

(10) Patent No.: US 12,213,888 B2
(45) Date of Patent: Feb. 4, 2025

(54) SYSTEM, APPARATUS, AND METHOD FOR ELBOW ARTHROPLASTY

(71) Applicants: James L. Cook, Columbia, MO (US); Trent M. Guess, Columbia, MO (US); Matthew J. Smith, Columbia, MO (US)

(72) Inventors: James L. Cook, Columbia, MO (US); Trent M. Guess, Columbia, MO (US); Matthew J. Smith, Columbia, MO (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 371 days.

(21) Appl. No.: 16/981,330

(22) PCT Filed: Mar. 22, 2019

(86) PCT No.: PCT/US2019/023615
§ 371 (c)(1),
(2) Date: Sep. 16, 2020

(87) PCT Pub. No.: WO2019/190923
PCT Pub. Date: Oct. 3, 2019

(65) Prior Publication Data
US 2021/0059824 A1    Mar. 4, 2021

Related U.S. Application Data

(60) Provisional application No. 62/650,480, filed on Mar. 30, 2018.

(51) Int. Cl.
*A61F 2/38*      (2006.01)
*A61F 2/30*      (2006.01)

(52) U.S. Cl.
CPC .. *A61F 2/3804* (2013.01); *A61F 2002/30253* (2013.01); *A61F 2002/3065* (2013.01);
(Continued)

(58) Field of Classification Search
CPC .......... A61F 2/3804; A61F 2002/30253; A61F 2002/3065; A61F 2002/30655;
(Continued)

(56) References Cited

U.S. PATENT DOCUMENTS 3,939,496 A * 2/1976 Ling ............... A61F 2/3804
                                                    623/20.12
5,879,395 A * 3/1999 Tornier ........... A61F 2/3804
                                                    623/20.13

(Continued)

FOREIGN PATENT DOCUMENTS

GB         1412376 A  * 11/1975  ........... A61F 2/4261

OTHER PUBLICATIONS

International Search Report and Written Opinion for related PCT/US2019/023615, dated Jun. 6, 2019 (11 pgs).

(Continued)

*Primary Examiner* — Megan Y Wolf
(74) *Attorney, Agent, or Firm* — STINSON LLP

(57) ABSTRACT

An elbow arthroplasty system having a ball and a socket. The ball is configured for coupling to at least one member of one of the following groups: (i) a humerus, and (ii) a radius, an ulna, or both of the radius and the ulna. The socket is configured for coupling to at least one member of the other of the following groups: (i) the humerus, and (ii) the radius, the ulna, or both of the radius and the ulna. The socket defines a cavity that is configured to receive at least a portion of the ball. The ball may be a spheroid, an ellipsoid, a sphere, or a portion of one of the foregoing with a convex surface. The socket may be configured with a concave surface that is (Continued)

spheroidal, ellipsoidal, or spherical and designed to mate with the ball. An elbow arthroplasty method using a ball and a socket.

29 Claims, 14 Drawing Sheets

(52) U.S. Cl.
CPC .............. *A61F 2002/30655* (2013.01); *A61F 2002/3809* (2013.01); *A61F 2002/3813* (2013.01)

(58) Field of Classification Search
CPC ...... A61F 2002/3809; A61F 2002/3813; A61F 2002/30649; A61F 2002/3818; A61F 2002/3822; A61F 2002/3827; A61F 2002/3831
See application file for complete search history.

(56) References Cited

U.S. PATENT DOCUMENTS

| | | | |
|---|---|---|---|
| 6,162,253 A * | 12/2000 | Conzemius | A61F 2/3804 623/20.11 |
| 6,306,171 B1 * | 10/2001 | Conzemius | A61F 2/3804 623/20.11 |
| 7,608,110 B2 * | 10/2009 | O'Driscoll | A61F 2/4657 623/20.11 |
| 2002/0165614 A1 * | 11/2002 | Tornier | A61F 2/3804 623/20.12 |
| 2003/0208277 A1 * | 11/2003 | Weiss | A61F 2/3804 623/20.12 |
| 2005/0085915 A1 * | 4/2005 | Steinberg | A61B 17/1684 623/23.72 |
| 2007/0244563 A1 | 10/2007 | Roche | |
| 2009/0254189 A1 | 8/2009 | Scheker | |
| 2012/0053697 A1 * | 3/2012 | Palmer | A61F 2/3804 623/20.12 |
| 2013/0103158 A1 * | 4/2013 | Linares | A61F 2/3804 623/20.11 |
| 2016/0296336 A1 | 10/2016 | Maale | |

OTHER PUBLICATIONS

Brochure, Zimmer Nexel Total Elbow Surgical Technique (34 pgs).
Product Information from Wayback Machine, Delta Xtend Reverse Shoulder System, DePuy Synthes Products, Aug. 12, 2016 (2 pgs).
Pooley, Unicompartmental Elbow Replacement: Development oa a Lateral Replacement Elbow (LRE) Arthroplasty, Techniques in Shoulder and Elbow Surgery, vol. 8, Issue 4, pp. 204-212, 2007 (12 pgs).

* cited by examiner

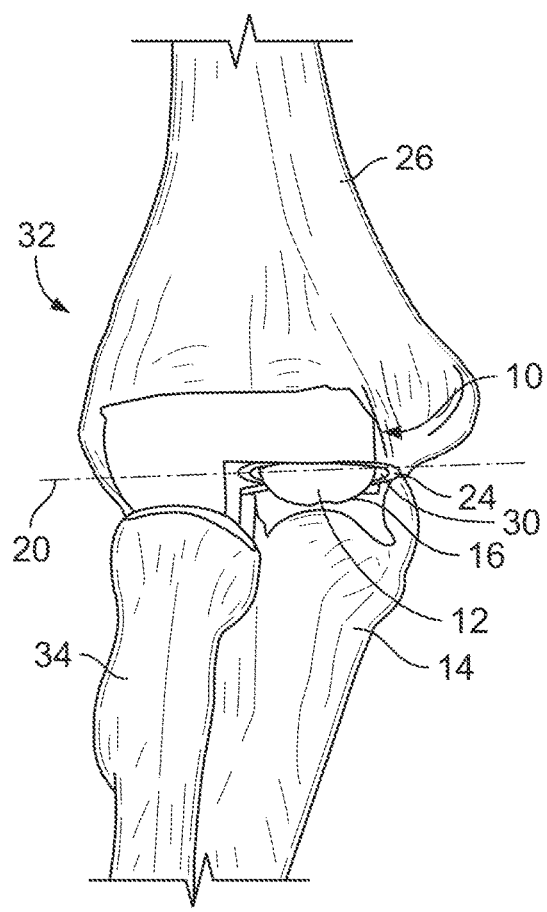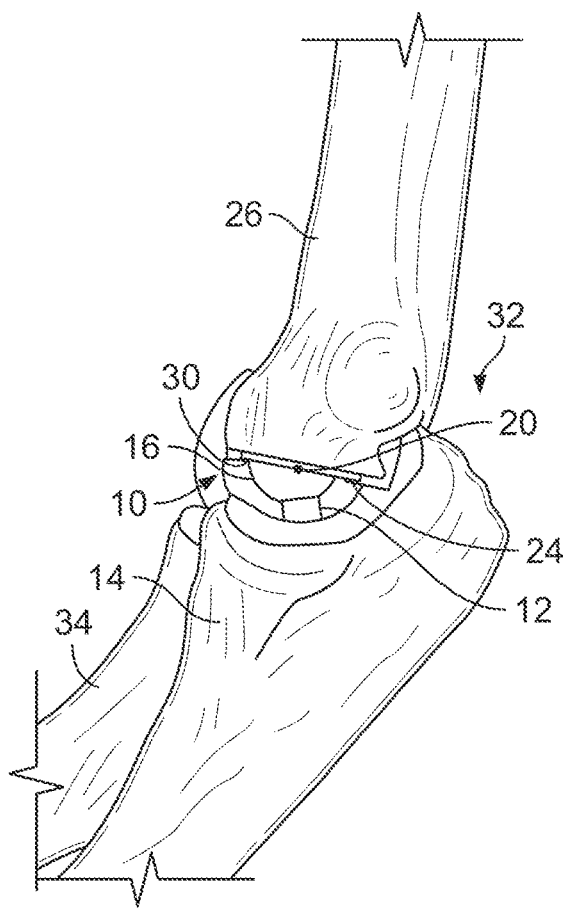
FIG. 3A  FIG. 3B
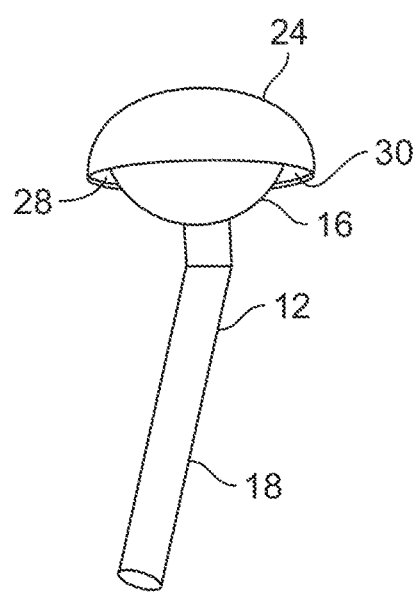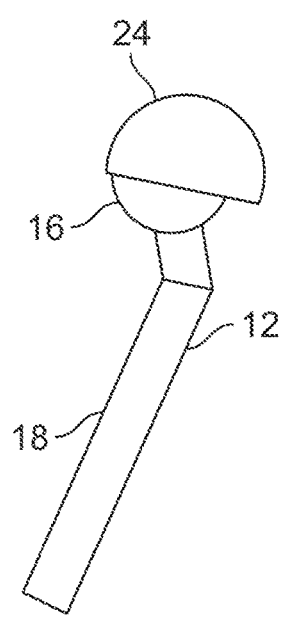
FIG. 3C  FIG. 3D

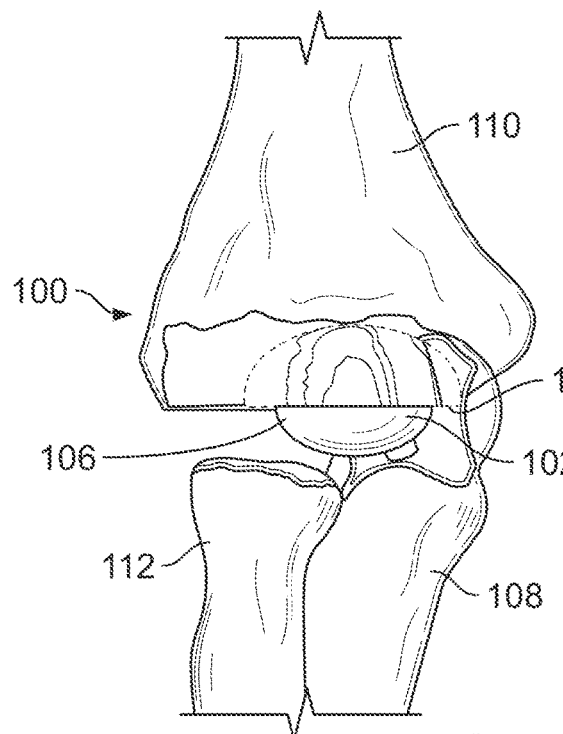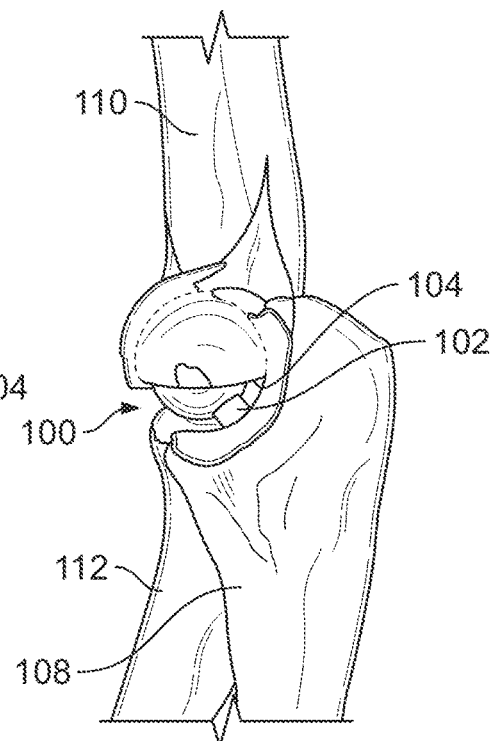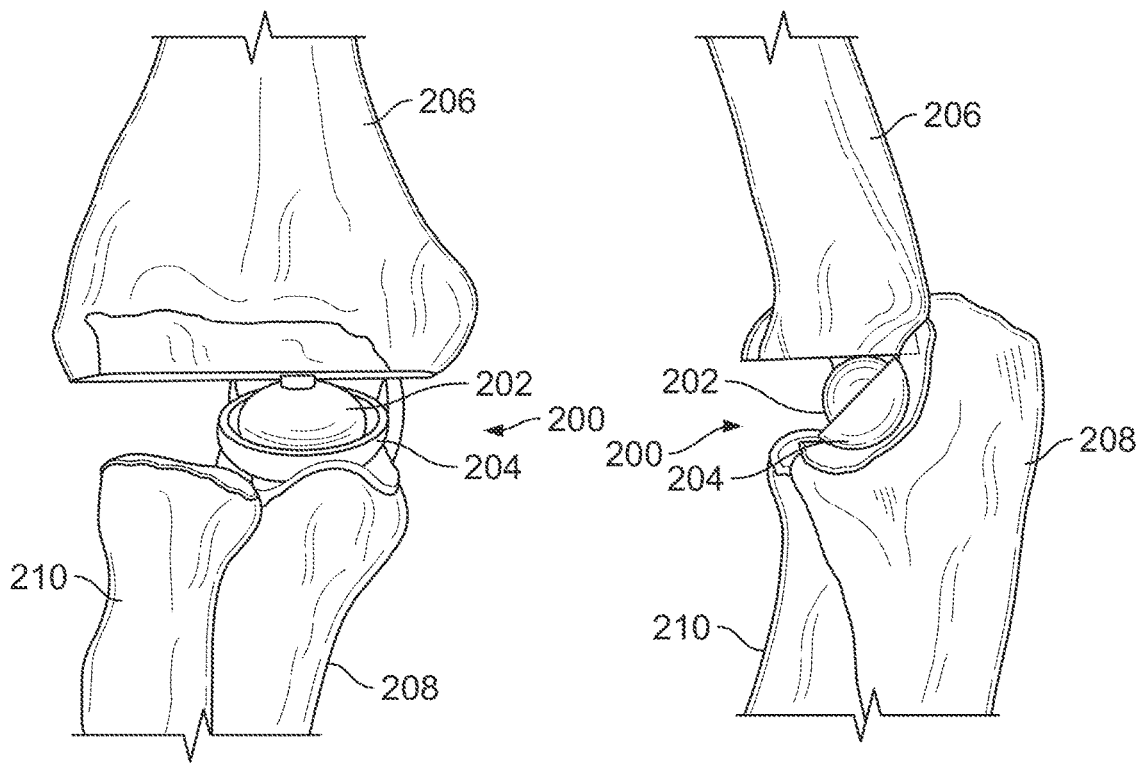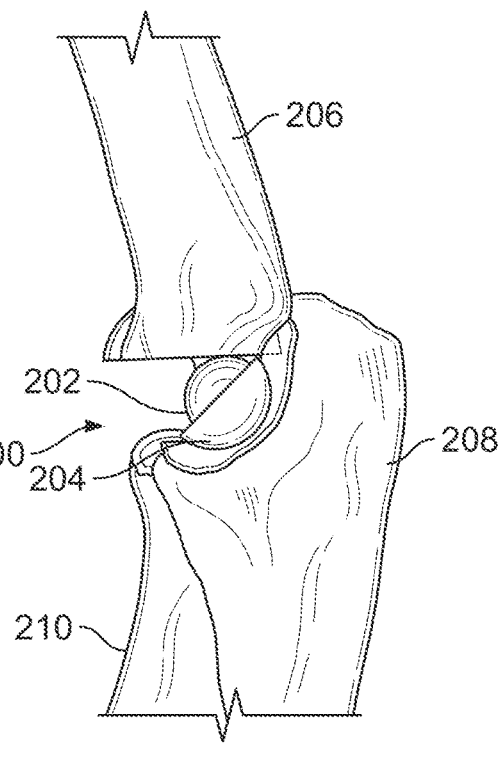
FIG. 4A  FIG. 4B
FIG. 5A  FIG. 5B

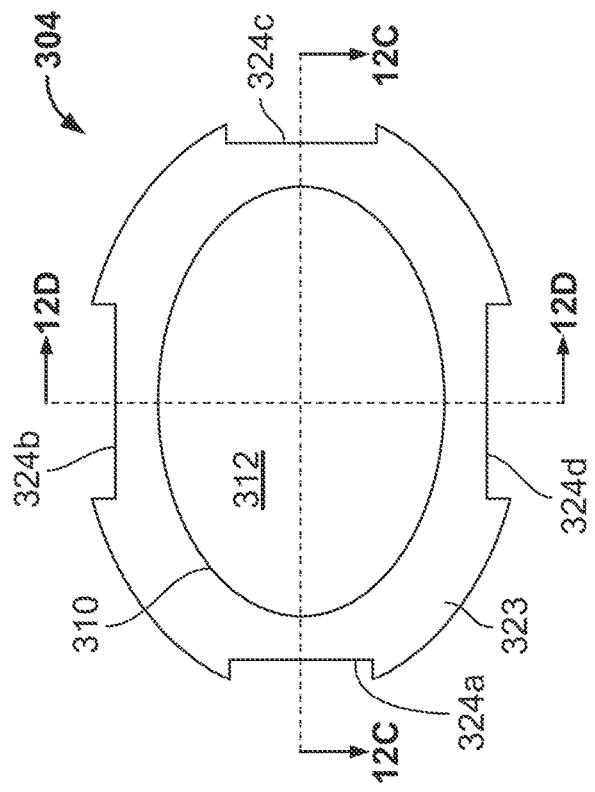
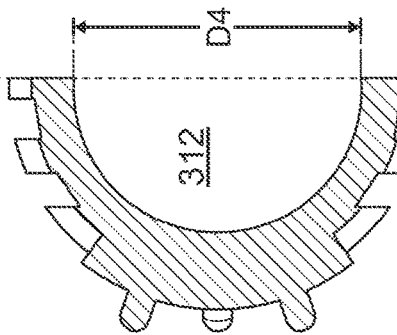
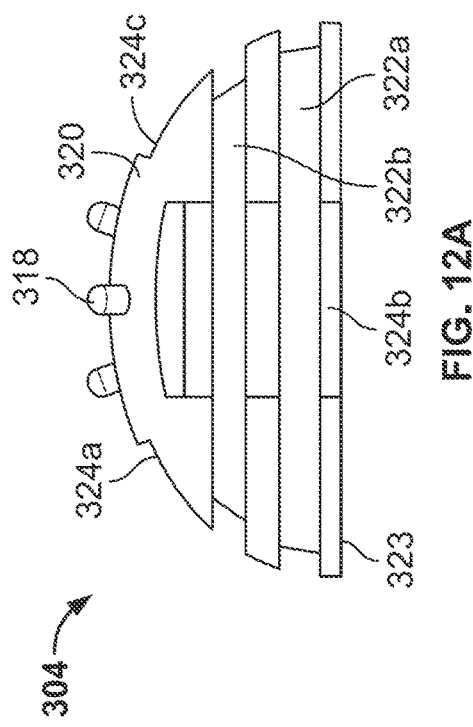
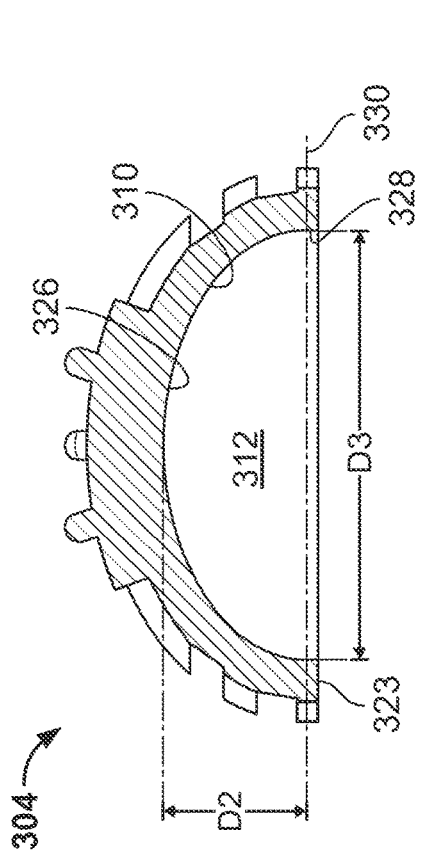

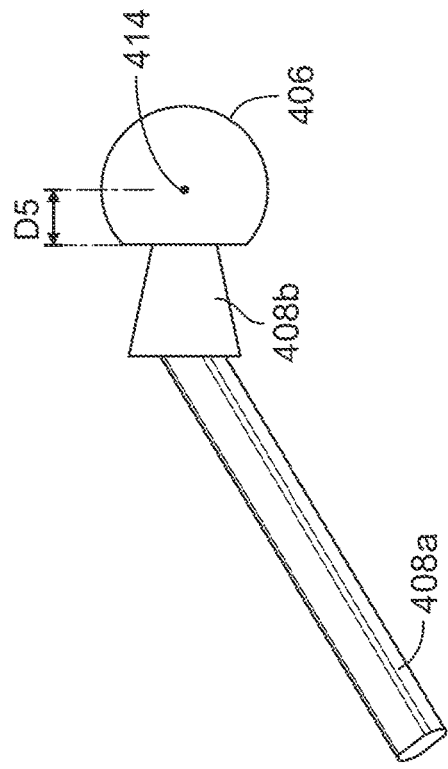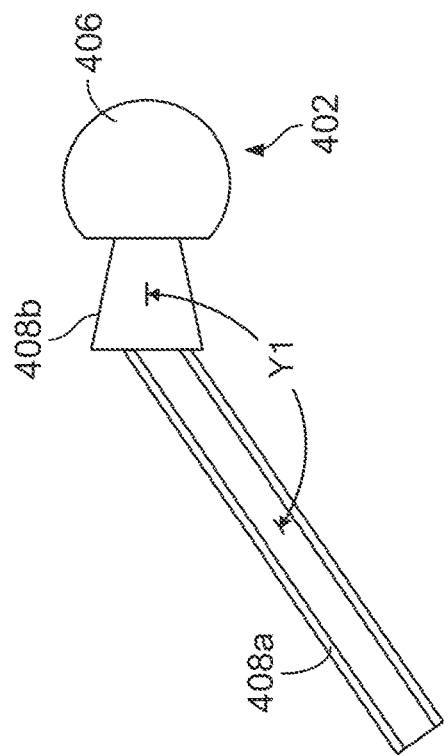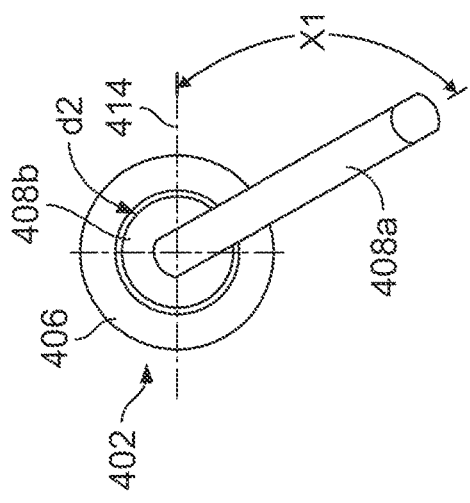

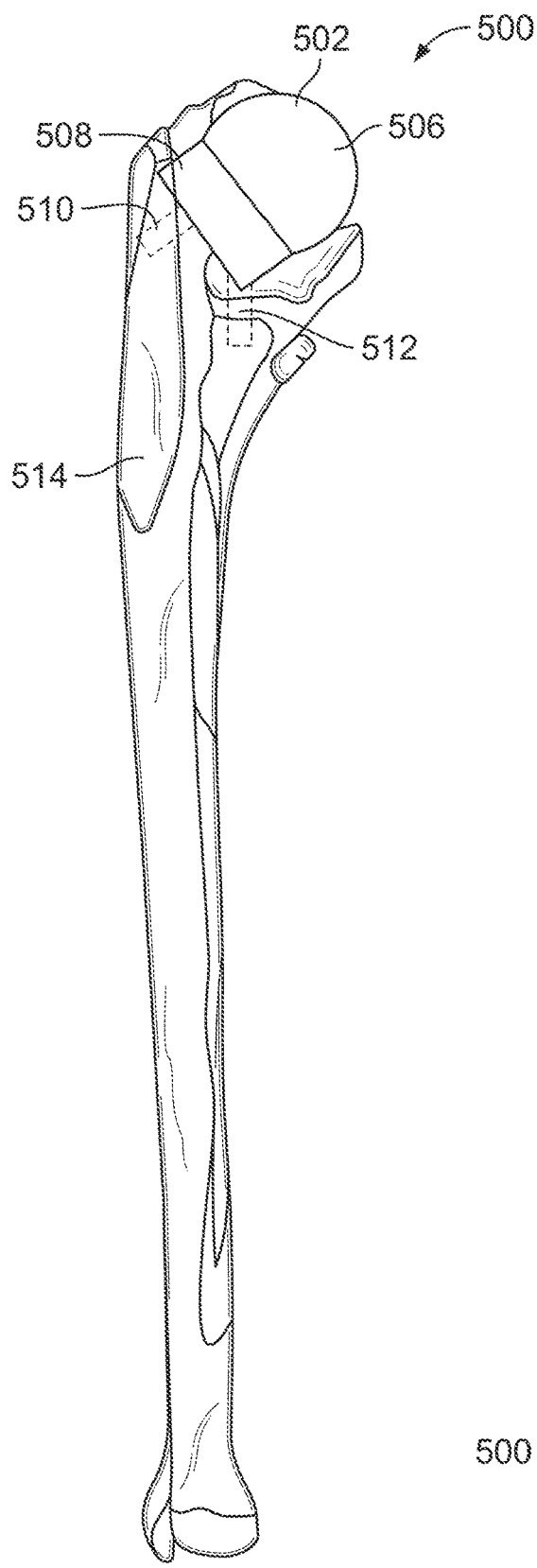
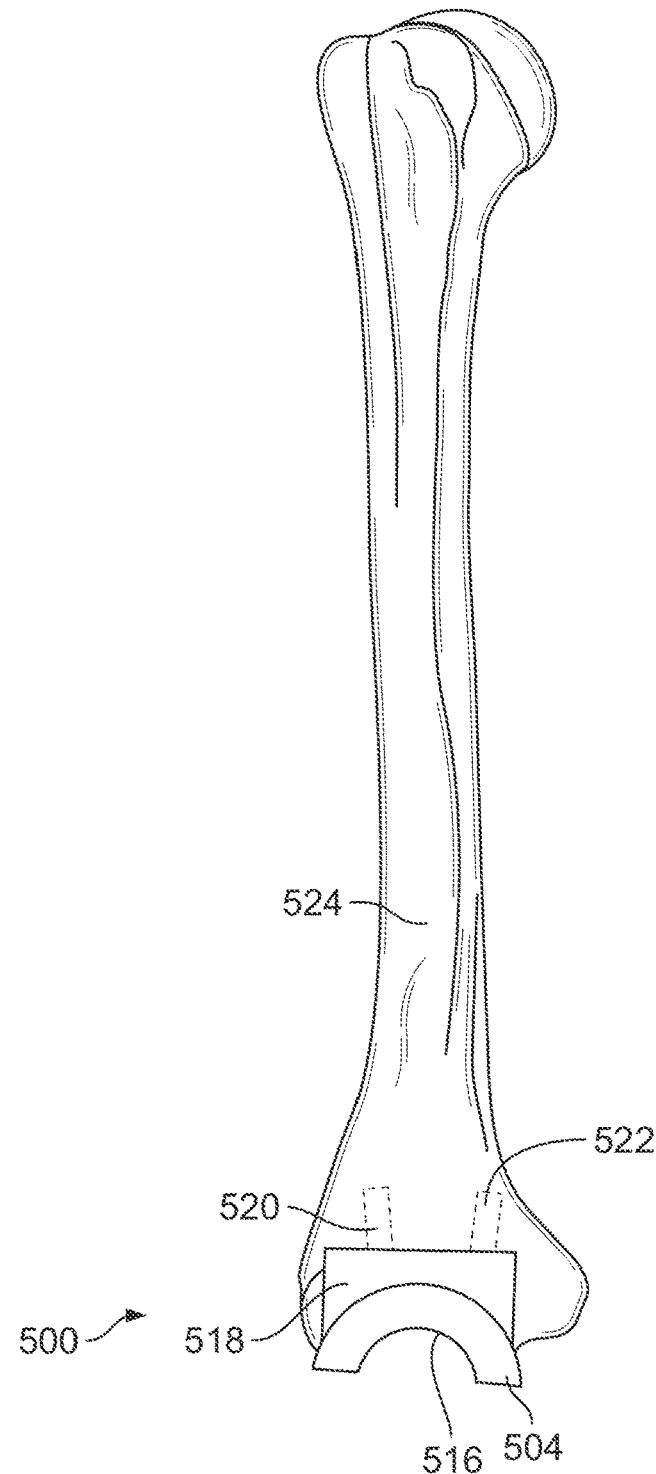
FIG. 16A
FIG. 16B

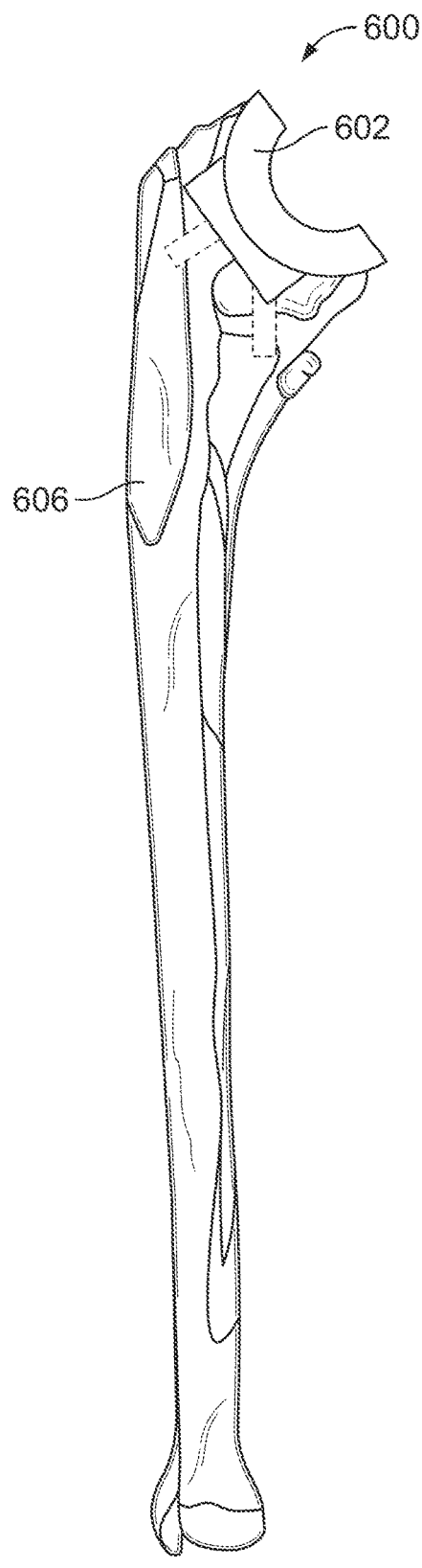
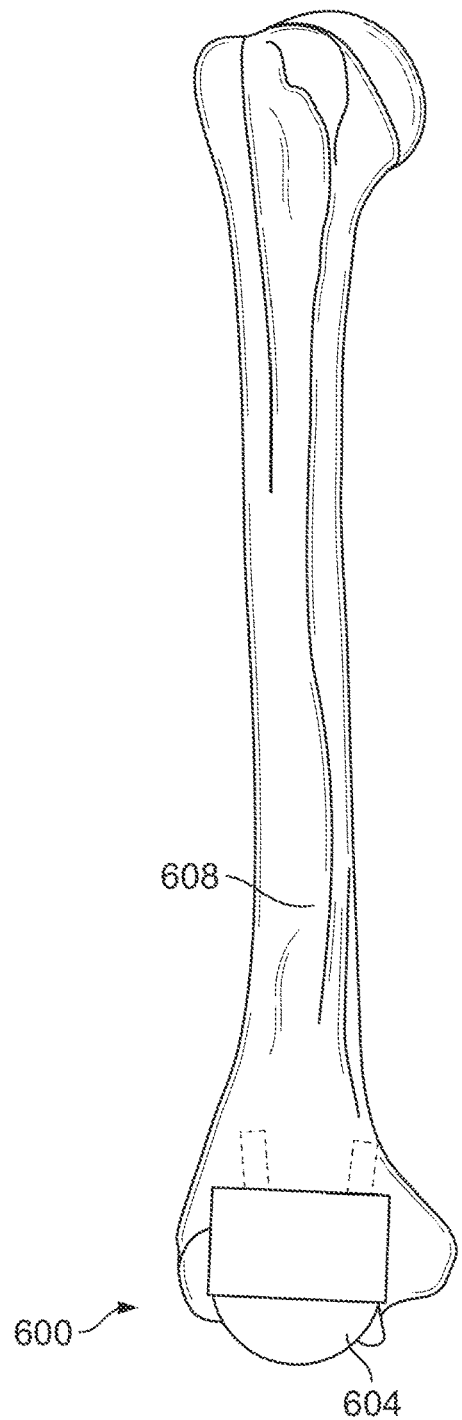
FIG. 17A
FIG. 17B

SYSTEM, APPARATUS, AND METHOD FOR ELBOW ARTHROPLASTY

CROSS-REFERENCE TO RELATED APPLICATIONS

This application is based on and claims priority to U.S. Provisional Application Ser. No. 62/650,480 filed on Mar. 30, 2018, which is hereby incorporated herein by reference.

BACKGROUND OF THE INVENTION

1. Field

This specification relates generally to systems, apparatus, and methods adapted for performing elbow arthroplasty.

2. Discussion

Total elbow arthroplasty is a surgical procedure included in the total joint replacement market. As the general population ages, the number of arthritis cases and elbow fractures is on the rise, which has created a need for a greater number of elbow replacement procedures. Although symptomatic arthritis of the elbow is less frequently diagnosed than in joints such as the knee or hip, the physical impairment of someone with arthritis in the elbow can be just as severe and greatly hinder a person's ability to work, enjoy recreational activities, and even perform activities of daily living. Conventional elbow replacement procedures utilize a hinge type joint. Current solutions for treating debilitating elbow joint problems have significant pitfalls, including significant loss of function with elbow joint fusion and high failure rates for standard hinge joint replacement.

BRIEF SUMMARY OF THE INVENTION

The invention described herein is a unique system for total elbow replacement that utilizes a spheroidal, ellipsoidal, or spherical ball-and-socket approach, as opposed to the standard hinge type replacement. The system can be implemented using two different ball-and-socket configurations, standard or reverse, to optimally treat each patient. This system is designed to provide improved safety, function, and longevity for elbow joint replacements versus other current treatment methods. Advantages of the elbow arthroplasty systems and methods described herein include: they are modular systems with standard and reverse configurations that allow patient- and disease-specific approaches to treatment; they have ball-and-socket type configurations; they restore complete range of motion to the elbow; and the surgical technique and instrumentation allows for greater post-operative stability than standard replacements.

An elbow arthroplasty system in accordance with one embodiment of the invention described herein includes a ball and a socket. The ball is configured for coupling to at least one member of one of the following groups: (i) a humerus, and (ii) a radius, an ulna, or both of the radius and the ulna. The socket is configured for coupling to at least one member of the other of the following groups: (i) the humerus, and (ii) the radius, the ulna, or both of the radius and the ulna. The socket defines a cavity that is configured to receive at least a portion of the ball. The ball may be a spheroid, an ellipsoid, a sphere, or a portion of one of the foregoing with a convex surface. The socket may be configured with a concave surface that is spheroidal, ellipsoidal, or spherical and designed to mate with the ball. The ball and the socket may be formed from a metal, a ceramic, a polymer, or any combination of the foregoing. A stem may be coupled to the ball. The stem and the socket may be configured to be coupled to at least one of a humerus, a radius, and an ulna using bone cement, a screw, a pin, press-fit fixation, or any combination of the foregoing. The stem may include a spacer that is configured to abut a bone when a portion of the stem is inserted in the bone for spacing the ball a desired distance from the bone.

In one embodiment, the socket is coupled to a distal portion of a humerus, and the ball is coupled to a proximal portion of an ulna, a proximal portion of a radius, or proximal portions of both the ulna and the radius. In another embodiment, the socket is coupled to a proximal portion of an ulna, a proximal portion of a radius, or proximal portions of both the ulna and the radius, and the ball is coupled to a distal portion of a humerus.

An elbow arthroplasty method in accordance with another embodiment of the invention described herein includes coupling a ball to at least one member of one of the following groups: (i) a humerus, and (ii) a radius, an ulna, or both of the radius and the ulna; coupling a socket to at least one member of the other of the following groups: (i) the humerus, and (ii) the radius, the ulna, or both of the radius and the ulna; and positioning at least a portion of the ball within a cavity defined by the socket. The ball may be a spheroidal or ellipsoidal (or a portion of one of the foregoing) and coupled with an ulna so that a major axis of the ellipsoid or spheroid is generally aligned with a radial center of a trochlear notch of the ulna. Further, the socket may be coupled with a humerus so that the major axis of the ellipsoidal ball is generally aligned with a center of rotation of the humerus trochlea when the ball is received in the cavity and articulates with the socket. The ball and the socket may be positioned with respect to the humerus and the ulna so that as the ball articulates with the socket the ulna rotates with respect to the humerus in a manner that is similar to natural humeroulnar articulation.

In one embodiment, provided is a system adapted for elbow arthroplasty in which a spheroidal, ellipsoidal, or spherical radial component that is modular in nature and is comprised of medical-grade metallic, ceramic, and/or polymer-based materials is surgically fitted to and affixed to the proximal radius using bone cement, screws, pins, and/or press-fit fixation; and a matching concave humeral component that is modular in nature and is comprised of medical-grade metallic, ceramic, and/or polymer-based materials is surgically fitted to and affixed to the distal humerus using bone cement, screws, pins, and/or press-fit fixation.

In another embodiment, provided is a system adapted for elbow arthroplasty in which a spheroidal, ellipsoidal, or spherical ulnar component that is modular in nature and is comprised of medical-grade metallic, ceramic, and/or polymer-based materials is surgically fitted to and affixed to the proximal ulnar using bone cement, screws, pins, and/or press-fit fixation; and a matching concave humeral component that is modular in nature and is comprised of medical-grade metallic, ceramic, and/or polymer-based materials is surgically fitted to and affixed to the distal humerus using bone cement, screws, pins, and/or press-fit fixation.

In yet another embodiment, provided is a system adapted for elbow arthroplasty in which a spheroidal, ellipsoidal, or spherical humeral component that is modular in nature and is comprised of medical-grade metallic, ceramic, and/or polymer-based materials is surgically fitted to and affixed to the distal humerus using bone cement, screws, pins, and/or press-fit fixation; and a matching concave radial component that is modular in nature and is comprised of medical-grade metallic, ceramic, and/or polymer-based materials is surgically fitted to and affixed to the proximal radius using bone cement, screws, pins, and/or press-fit fixation.

In yet another embodiment, provided is a system adapted for elbow arthroplasty in which a spheroidal, ellipsoidal, or spherical humeral component that is modular in nature and is comprised of medical-grade metallic, ceramic, and/or polymer-based materials is surgically fitted to and affixed to the distal humerus using bone cement, screws, pins, and/or press-fit fixation; and a matching concave ulnar component that is modular in nature and is comprised of medical-grade metallic, ceramic, and/or polymer-based materials is surgically fitted to and affixed to the proximal ulna using bone cement, screws, pins, and/or press-fit fixation.

In yet another embodiment, provided is a system adapted for elbow arthroplasty in which a spheroidal, ellipsoidal, or spherical humeral component that is modular in nature and is comprised of medical-grade metallic, ceramic, and/or polymer-based materials is surgically fitted to and affixed to the distal humerus using bone cement, screws, pins, and/or press-fit fixation; and a matching concave radio-ulnar component that is modular in nature and is comprised of medical-grade metallic, ceramic, and/or polymer-based materials is surgically fitted to and affixed to the proximal radius and ulna using bone cement, screws, pins, and/or press-fit fixation.

In yet another embodiment, provided is a system adapted for elbow arthroplasty in which a spheroidal, ellipsoidal, or spherical radio-ulnar component that is modular in nature and is comprised of medical-grade metallic, ceramic, and/or polymer-based materials is surgically fitted to and affixed to the proximal radius and ulna using bone cement, screws, pins, and/or press-fit fixation; and a matching concave humeral component that is modular in nature and is comprised of medical-grade metallic, ceramic, and/or polymer-based materials is surgically fitted to and affixed to the distal humerus using bone cement, screws, pins, and/or press-fit fixation.

The provision of such systems described above, which are configured to replace an elbow, are firmly secure, have positional guides for implantation at selected locations (e.g., external cutting guides and templates for preparing the bone for implantation and estimating the size and position of the implant), allow for implantation with minimal invasiveness to ligaments and soft tissues surrounding the elbow, and allow for normal or near-normal joint function.

Other objects, features, and advantages of the illustrative embodiments will become apparent with reference to the drawings and detailed description that follow.

BRIEF DESCRIPTION OF THE DRAWINGS

FIGS. 3A-3B are frontal and side views, respectively, of an elbow with the elbow arthroplasty system shown in FIGS. 1A-2B replacing the humeroulnar joint.

FIGS. 3C-3D are frontal and side views, respectively, of the convex prosthetic component of FIGS. 1A-B mated with the concave prosthetic component of FIGS. 2A-B.

FIGS. 4A-4B are frontal and side views, respectively, of an elbow with an alternative embodiment of elbow arthroplasty system that replaces the humeroradial joint and the humeroulnar joint.

FIGS. 5A-5B are frontal and side views, respectively, of an elbow with an alternative embodiment of elbow arthroplasty system replacing the humeroradial joint and the humeroulnar joint. The elbow arthroplasty system has a concave prosthetic component joined to a proximal portion of an ulna and an convex prosthetic component joined to a distal portion of a humerus.

FIG. 12A is a side elevational view of a concave prosthetic component of the elbow arthroplasty system shown in FIG. 10.

FIG. 12B is a top plan view of the concave prosthetic component shown in FIG. 12A.

FIG. 12C is a cross-sectional view taken through the line 12C-12C of FIG. 12B.

FIG. 12D is a cross-sectional view taken through the line 12D-12D of FIG. 12B.

FIG. 14A is a bottom plan view of a convex prosthetic component of the elbow arthroplasty system shown in FIG. 13.

FIG. 14B is a side elevational view of the convex prosthetic component shown in FIG. 14A.

FIG. 14C is a side elevational view of the convex prosthetic component shown in FIG. 14A that is rotated slightly downward relative to the view shown in FIG. 14B.

FIG. 16A is a side view of a convex prosthetic component of an alternative embodiment of elbow arthroplasty system. The convex prosthetic component is shown surgically attached to a proximal portion of an ulna.

FIG. 16B is a front view of a concave prosthetic component for use with the convex prosthetic component shown in FIG. 16A. The concave prosthetic component is shown surgically attached to a distal portion of a humerus.

FIG. 17A is a side view of a concave prosthetic component of an alternative embodiment of elbow arthroplasty system. The concave prosthetic component is shown surgically attached to a proximal portion of an ulna.

FIG. 17B is a front view of a convex prosthetic component for use with the concave prosthetic component shown in FIG. 17A. The convex prosthetic component is shown surgically attached to a distal portion of a humerus.

DETAILED DESCRIPTION OF PREFERRED EMBODIMENT

In the following detailed description, reference is made to the accompanying drawings that depict by way of illustration specific embodiments for practicing the subject matter disclosed in this specification. These embodiments are described in sufficient detail to enable those skilled in the art to practice the subject matter of this specification. Other embodiments may be utilized and logical structural, mechanical, electrical, and chemical changes may be made without departing from the scope of this specification. To avoid detail not necessary to enable those skilled in the art to practice the embodiments described herein, the description may omit certain information known to those skilled in the art. The following detailed description is, therefore, not to be taken in a limiting sense, with the scope of the illustrative embodiments being defined by the appended claims.

Figure 1A:
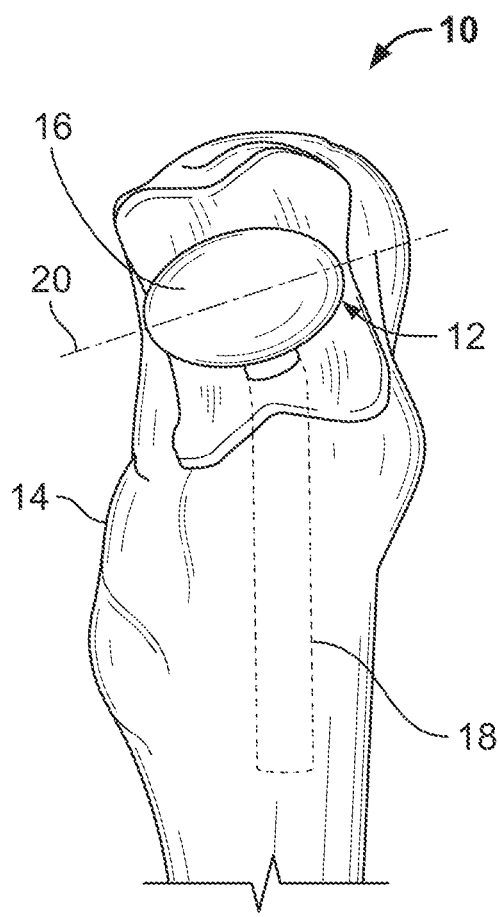
FIG. 1A is a frontal view of a convex prosthetic component of an elbow arthroplasty system in accordance with one embodiment of the invention described herein. The convex prosthetic component has an ellipsoidal ball and is shown surgically attached to a proximal portion of an ulna.
Figure 1B:
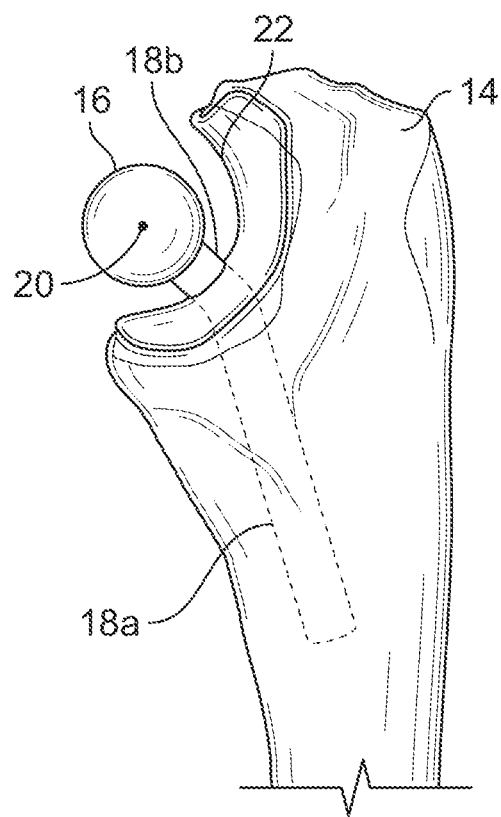
FIG. 1B is a side view of the convex prosthetic component shown in FIG. 1A.

Referring to FIGS. 1A-1B, one embodiment of elbow arthroplasty system 10 in accordance with the invention described herein includes a convex prosthetic component 12, which is shown surgically attached to a proximal portion of an ulna 14. Convex prosthetic component 12 is modular in nature and may be formed from medical-grade metallic, ceramic, and/or polymer-based materials. Convex prosthetic component 12 includes a ball 16 and a stem 18 that is surgically fitted to and affixed to the proximal ulna 14 preferably using bone cement, screws, pins, and/or press-fit fixation. Convex prosthetic component 12 may be cemented to ulna 14 or un-cemented with porous or bone ingrowth. Ball 16 is an ellipsoid with a major axis 20. Ball 16 is joined to an end of stem 18. Stem 18 includes a first section 18a that extends into a cavity formed in the ulna 14 and a second section 18b that extends from first section 18a away from ulna 14. Ball 16 and stem 18 are configured so that when first section 18a is positioned within ulna 14, ball 16 is positioned with respect to ulna 14 so that major axis 20 of ball 16 is generally aligned with a radial center of a trochlear notch 22 of ulna 14. Stem 18 may include a positional guide or spacer that abuts ulna 14 when first section 18a is inserted in ulna 14 to space ball 16 from ulna 14 the desired distance.

Figure 2A:
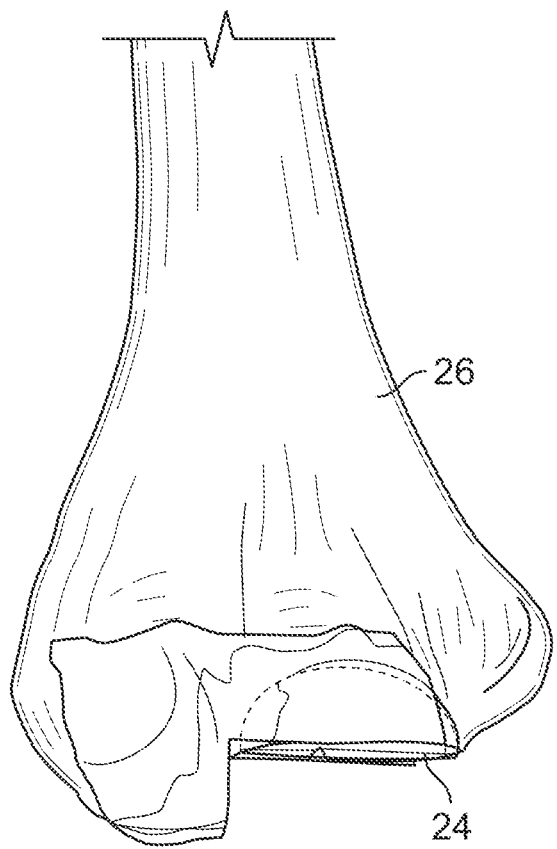
FIGS. 2A-2B are frontal and side views, respectively, of a concave prosthetic component of the elbow arthroplasty system shown in FIGS. 1A-B. The concave prosthetic component is shown surgically attached to a distal portion of a humerus and is configured to receive the convex prosthetic component shown in FIGS. 1A-B.
Figure 2B:
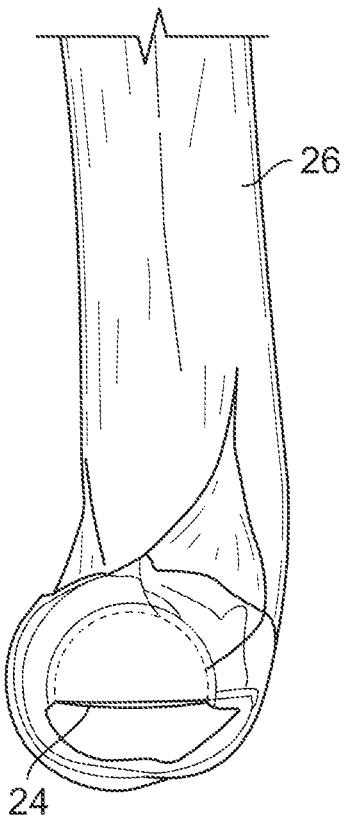

As shown in FIGS. 2A-2B, elbow arthroplasty system 10 further includes a concave prosthetic component, or socket, 24, which is shown surgically attached to a distal portion of a humerus 26. Concave prosthetic component 24 is modular in nature and may be formed from medical-grade metallic, ceramic, and/or polymer-based materials. Concave prosthetic component 24 is surgically fitted to and affixed to the distal humerus 26 preferably using bone cement, screws, pins, and/or press-fit fixation. Concave prosthetic component 24 may be cemented to ulna 14 or un-cemented with porous or bone ingrowth. Concave prosthetic component 24 has a concave ellipsoidal surface 28 (FIG. 3C) that defines a cavity 30 configured for receiving a portion of ball 16. The trochlea of humerus is 26 is removed and a cavity is formed in humerus 26 for receiving concave prosthetic component 24.

FIGS. 3A-3B show an elbow 32 that includes elbow arthroplasty system 10. Elbow arthroplasty system 10 replaces the humeroulnar joint of elbow 32. Ball 16 is positioned within cavity 30 to mate convex prosthetic component 12 with concave prosthetic component 24, as best shown in FIGS. 3C-3D, which show elbow arthroplasty system 10 without ulna 14 and humerus 26. The mating convex and concave prosthetic components 12 and 24 allow movement of ulna 14 relative to humerus 26. During movement of ulna 14 relative to humerus 26, convex prosthetic component 12 articulates with the matching concave prosthetic component 24. Concave prosthetic component 24 is positioned with respect to humerus 26 so that major axis 20 of ball 16 is generally aligned with a center of rotation of a trochlea of humerus 26. Ball 16 and concave prosthetic component 24 are positioned with respect to ulna 14 and humerus 26 so that as ball 16 articulates with concave prosthetic component 24, ulna 14 moves with respect to humerus 26 in a manner that is similar to natural humeroulnar articulation.

Convex prosthetic component 12 may alternatively be attached to a proximal portion of radius 34 or to proximal portions of both ulna 14 and radius 34. Further, convex and concave prosthetic components 12 and 24 may be spherical or spheroidal.

Referring to FIGS. 4A-B, an alternative embodiment of elbow arthroplasty system is generally identified as 100. Elbow arthroplasty system 100 is substantially similar to elbow arthroplasty system 10 except that it replaces both the humeroulnar joint and the humeroradial joint. Like elbow arthroplasty system 10, elbow arthroplasty system 100 includes a convex prosthetic component 102 that mates with a concave prosthetic component, or socket, 104. Convex prosthetic component 102 includes an ellipsoidal ball 106 and a stem (not shown) that is surgically attached to a proximal portion of an ulna 108. Concave prosthetic component 104 has a concave ellipsoidal surface defining a cavity configured to receive ball 106. Concave prosthetic component 104 is surgically attached to a distal portion of a humerus 110. Ball 106 and concave prosthetic component 104 may be slightly larger than the ball 16 and concave prosthetic component 24 shown in FIGS. 3A-3B so that elbow arthroplasty system 100 is configured to replace both the humeroulnar joint (i.e., the joint between humerus 110 and ulna 108) and the humeroradial joint (i.e., the joint between humerus 110 and radius 112). Convex prosthetic component 102 may alternatively be attached to a proximal portion of radius 112 or to proximal portions of both ulna 108 and radius 112. Convex and concave prosthetic components 102 and 104 may be spherical or spheroidal. Other than the differences described above, elbow arthroplasty system 100 is preferably configured substantially similar to elbow arthroplasty system 10.

FIGS. 5A-B show another alternative embodiment of elbow arthroplasty system generally identified as 200. Elbow arthroplasty system 200 is similar to elbow arthroplasty system 100 in that it also replaces the humeroulnar and humeroradial joints. Elbow arthroplasty system 200 is further similar to elbow arthroplasty systems 10 and 100 except that the convex and concave prosthetic components 202 and 204 are reversed. Convex prosthetic component 202 is surgically attached to a distal portion of a humerus 206, and concave prosthetic component, or socket, 204 is surgically attached to a proximal portion of an ulna 208. Concave prosthetic component 204 may alternatively be attached to a proximal portion of radius 210 or to proximal portions of both ulna 208 and radius 210. Convex and concave prosthetic components 202 and 204 may be spherical or spheroidal. Other than the differences described above, elbow arthroplasty system 200 is preferably configured substantially similar to elbow arthroplasty systems 10 and 100.

Experimental Results

Figure 6:
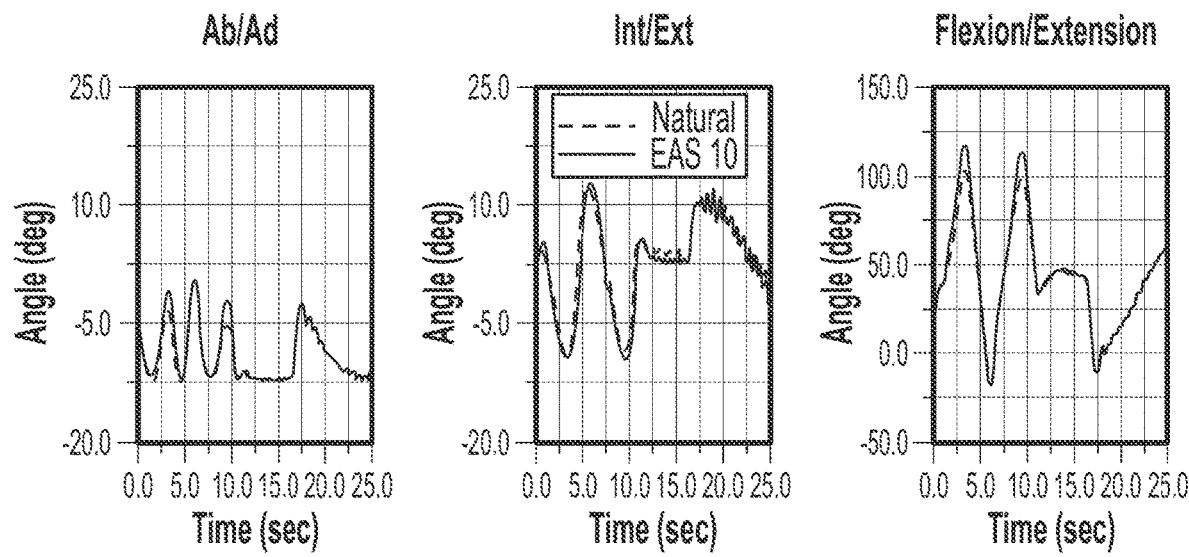
FIG. 6 is a series of graphs showing abduction/adduction, internal/external, and flexion/extension rotation of the ulna relative to the humerus for a natural elbow ("Natural") and for the elbow arthroplasty system ("EAS 10") described herein.
Figure 7:
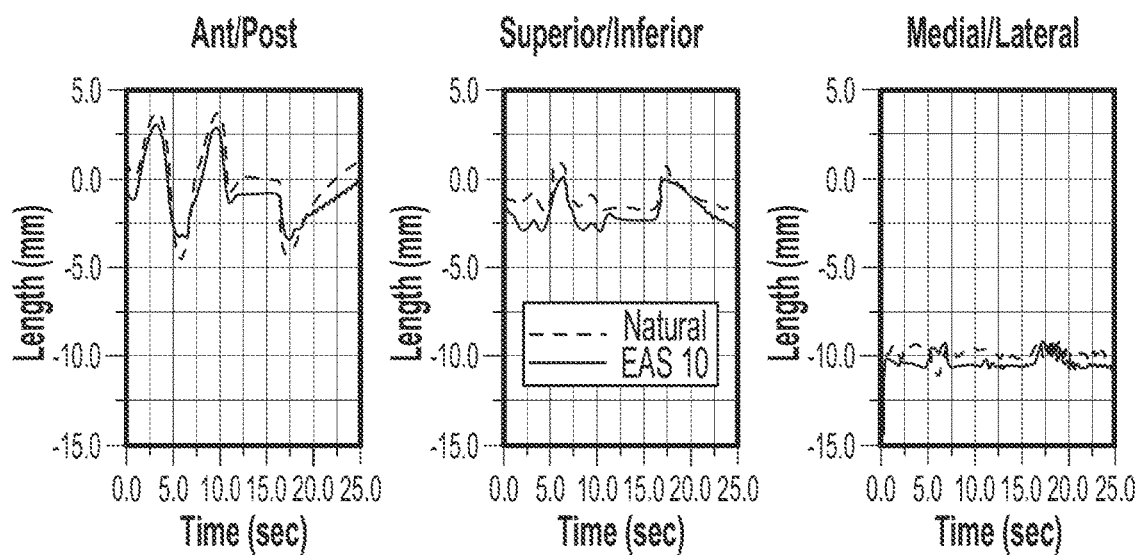
FIG. 7 is a series of graphs showing anterior/posterior, superior/inferior, and medial/lateral translation of the ulna relative to the humerus for a natural elbow and for the elbow arthroplasty system described herein.
Figure 8:
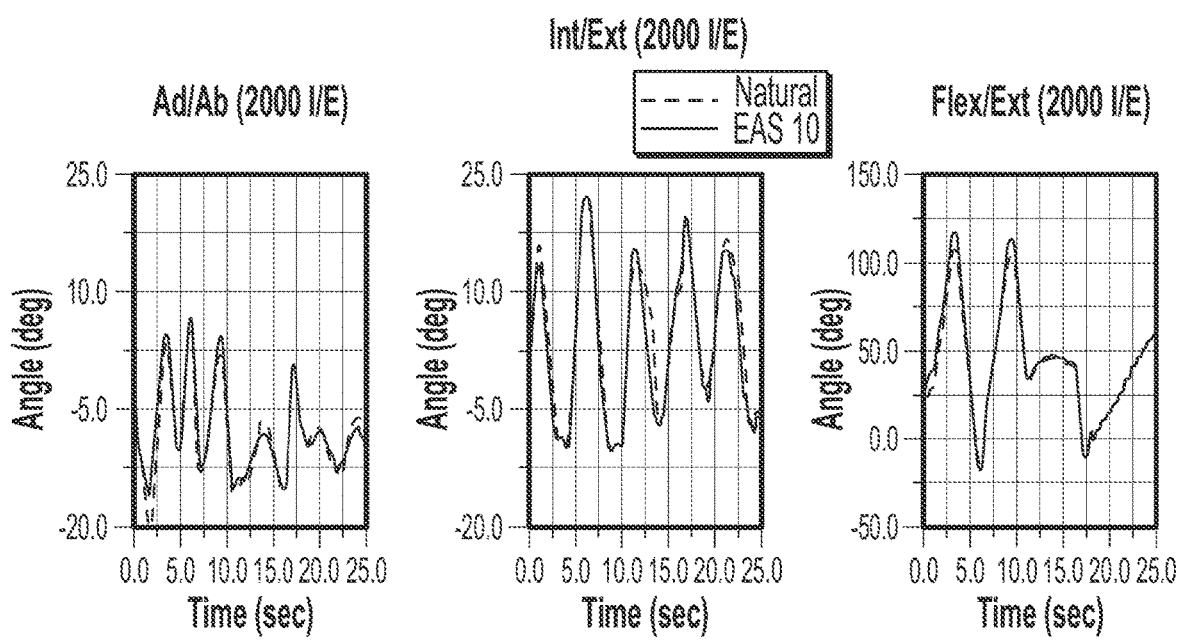
FIG. 8 is a series of graphs showing abduction/adduction, internal/external, and flexion/extension rotation of the ulna relative to the humerus similar to FIG. 6 but with an additional internal/external torque applied to the ulna.
Figure 9:
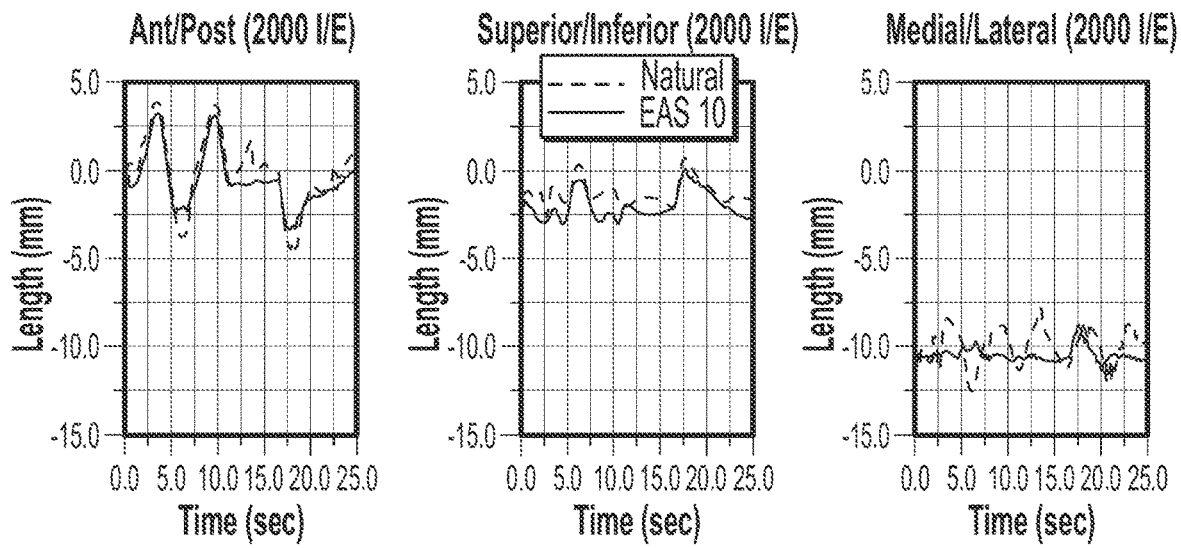
FIG. 9 is a series of graphs showing anterior/posterior, superior/inferior, and medial/lateral translation of the ulna relative to the humerus similar to FIG. 7 but with an additional internal/external torque applied to the ulna.

The ball-and-socket approach of elbow arthroplasty systems 10, 100, and 200 provides geometric constraints that mimic the natural constraint provided by articulation of the humerus trochlea and the ulna trochlear groove. Referring to FIGS. 6-9, arthrokinematic motion of elbow arthroplasty system 10 with an ellipsoidal convex prosthetic component attached to the ulna and a matching concave ellipsoidal prosthetic component attached to the humerus is similar to that of a natural elbow. FIG. 6 shows abduction/adduction, internal/external, and flexion/extension rotation of the ulna relative to the humerus for a natural elbow and for the elbow arthroplasty system 10. The data for FIG. 6 comes from optical motion measurements of a cadaver arm combined with computational simulations that included contact between articulating cartilage surfaces and ligaments. For the cadaver measurements, the humerus was fixed while the ulna was moved through its passive range of motion. A computational model was created specific to the measured cadaver arm and forces were applied in silico to the ulna such that experimentally measured ulna motion was reproduced. The dashed line in FIG. 6 labeled "Natural" shows these measurements. The natural humeral-ulnar joint was replaced by elbow arthroplasty system 10 and the same motion forces were applied to the ulna. The solid line in FIG. 6 labeled "EAS 10" shows these measurements. Where the dashed line is not shown in the drawings, it is substantially overlapped by the solid line. FIG. 7 shows anterior/posterior, superior/inferior, and medial/lateral translation of the ulna relative to the humerus, for 25 seconds of simulation, for the natural elbow (dashed line) and elbow arthroplasty system 10 (solid line). FIGS. 8-9 show relative rotation and relative translation of the ulna relative to the humerus for the applied motion forces of FIGS. 6-7 with an additional internal/external torque applied to the ulna. The applied torque was sinusoidal with a magnitude of 2000 N-mm. Measurements for the natural elbow are shown in dashed lines and for the elbow arthroplasty system 10 in solid lines. Elbow arthroplasty systems 10 and 300 (FIG. 10) preferably have similar structures and geometries, and as such, elbow arthroplasty system 300 preferably functions in substantially the same manner as shown in FIGS. 6-9 to mimic the biomechanics and geometric constraints of a natural elbow. Elbow arthroplasty systems 100, 200, 400 (FIG. 13), 500 (FIGS. 16A-B), and 600 (FIGS. 17A-B) may be configured to function in a different manner than as shown in FIGS. 6-9.

Figure 10:
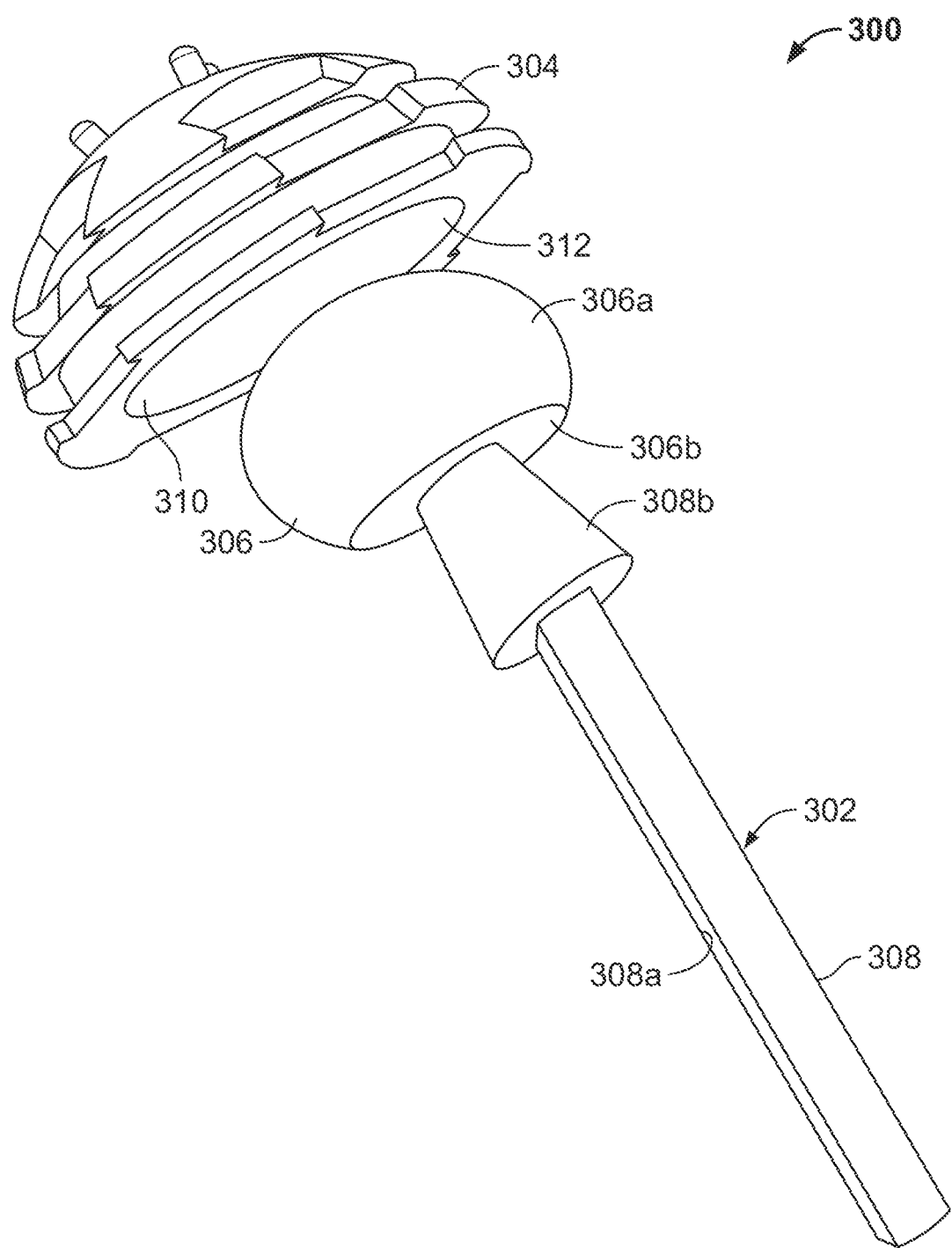
FIG. 10 is a perspective view of an alternative embodiment of elbow arthroplasty system having ellipsoidal prosthetic components.

Referring to FIG. 10, an alternative embodiment of elbow arthroplasty system is generally identified as 300. Elbow arthroplasty system 300 includes a convex prosthetic component 302 and a concave prosthetic component, or socket, 304. Convex prosthetic component 302 includes a ball 306 that is a portion of an ellipsoid and is joined to an end of a stem 308. Ball 306 is a truncated ellipsoid with an ellipsoidal outer surface 306a and a flat surface 306b that is joined to stem 308. Stem 308 includes a first section 308a and a second section 308b. First section 308a is an elongate rod with a cross-section that is generally rectangular with rounded ends. Second section 308b is shaped as a conical frustum tapering in size from first section 308a toward ball 306. First section 308a of stem 308 may be surgically attached to a proximal portion of an ulna in a similar manner as shown in FIGS. 1A-1B for stem 18. Alternatively, stem 308 may be surgically attached to a proximal portion of a radius, proximal portions of a radius and an ulna, or a distal portion of a humerus. Second section 308b may abut a portion of an ulna, radius, or humerus when first section 308a is inserted in a hole in the ulna, radius, or humerus to position ball 306 in a desired location with respect to the ulna, radius, or humerus. For example, second section 308b may abut the ulna, radius, or humerus to position ball 306 with respect to an ulna so that major axis 314 (FIGS. 11A-B) of ball 306 is generally aligned with a radial center of a trochlear notch of the ulna. In this manner, second section 308b acts as a spacer or positional guide that spaces ball 306 a desired distance from the ulna.

Concave prosthetic component 304 has a concave ellipsoidal surface 310 that defines a cavity 312 for receiving a portion of ball 306. Concave prosthetic component 304 may be surgically attached to a distal portion of a humerus in a similar manner as shown in FIGS. 2A-2B for concave prosthetic component 24. Alternatively, concave prosthetic component 304 may be surgically attached to a proximal portion of an ulna, a proximal portion of a radius, or proximal portions of a radius and an ulna. Convex and concave prosthetic components 302 and 304 mate and articulate with each other in a similar manner as described above for elbow arthroplasty systems 10, 100, and 200 such that elbow arthroplasty system 300 mimics the natural articulation of an elbow when in use.

Figure 11B:
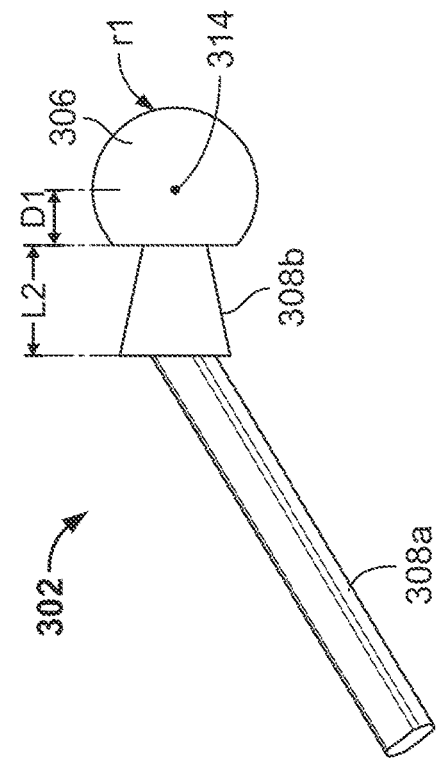
FIG. 11B is a side elevational view of the convex prosthetic component shown in FIG. 11A.
Figure 11C:
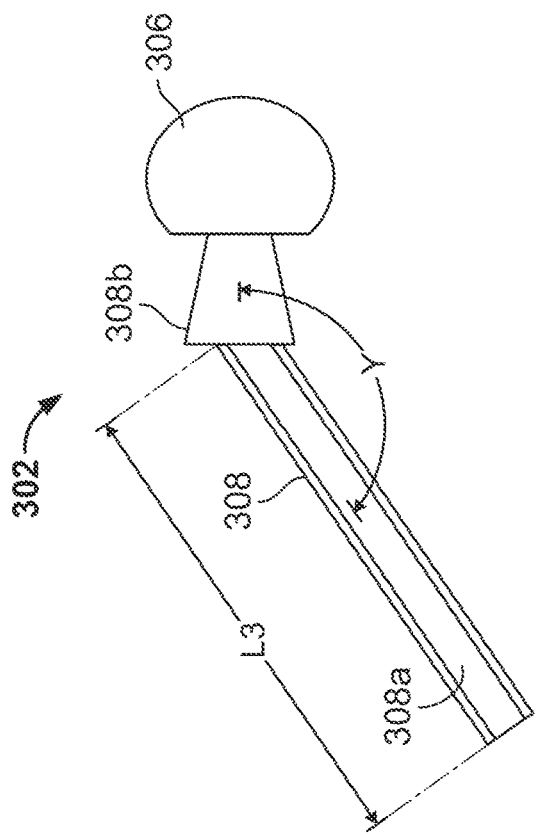
FIG. 11C is a side elevational view of the convex prosthetic component shown in FIG. 11A that is rotated slightly downward relative to the view shown in FIG. 11B.
Figure 11A:
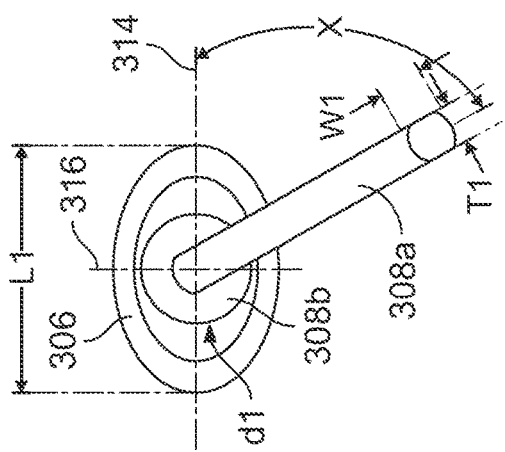
FIG. 11A is a bottom plan view of a convex prosthetic component of the elbow arthroplasty system shown in FIG. 10.

As shown in FIG. 11A, there is an angle X between a major axis 314 of ellipsoidal ball 306 and first section 308a of stem 308. Angle X may be between 56 to 66 degrees, is more preferably between 59 to 63 degrees, and is most preferably approximately 61 degrees. The diameter d1 of second section 308b where it is joined to first section 308a may be approximately 8 mm. The length L1 of ball 306 along its major axis 314 may be approximately 18 mm. The width W1 of first section 308a may be approximately 4 mm, and the thickness T1 of first section 308a may be approximately 3 mm.

As shown in FIG. 11B, the radius r1 of ball 306 at a cross-section taken through its minor axis 316 may be approximately 6 mm. The length L2 of second section 308b from first section 308a to ball 306 may be approximately 8 mm. The distance D1 from second section 308b to the major axis 314 may be approximately 4 mm. The combination of L2 and D1, which is preferably approximately 12 mm, represents the distance from the bone to the major axis 314 of ball 306 when first section 308a of stem 308 is inserted into the bone.

As shown in FIG. 11C, there is an angle Y between first section 308a of stem 308 and a central axis of the second section 308b of stem 308. Angle Y may be between 141 to 151 degrees, is more preferably between 144 to 148 degrees, and is most preferably approximately 146 degrees. The length L3 of first section 308a may be approximately 35 mm. The outer surface of second section 308b may taper at an angle of approximately 12 degrees from first section 308a to ball 306.

The angles X and Y and other dimensions referenced above preferably allow first section 308a to be securely attached to an ulna, a radius, an ulna and a radius, or a humerus, and ball 306 to be positioned so that articulation of elbow arthroplasty system 300 is similar to a natural elbow.

Referring to FIGS. 12A-D, concave prosthetic component 304 is generally a truncated ellipsoid with a hollow center that forms cavity 312. A plurality of protrusions (one of which is identified as 318) extend outward from an apex of an outer surface 320. Further, two circumferential grooves 322a-b extend around outer surface 320. Grooves 322a-b extend around outer surface 320 in planes oriented with a truncated surface 323 of concave prosthetic component 304. Notches 324a-d are further formed in outer surface 320, as shown in FIG. 12B. As shown in FIGS. 12A-B, notches 324a-d extend upward from truncated surface 323 approximately two-thirds of the way up toward the apex of outer surface 320. Notches 324a and 324c are oriented along a major axis of concave prosthetic component 304, and notches 324b and 324d are oriented along a minor axis of concave prosthetic component 304. Protrusions 318, grooves 322a-b, and notches 324a-d preferably aid in surgically attaching concave prosthetic component 304 to an ulna, radius, or humerus. For example, protrusions 318, grooves 322a-b, and notches 324a-d provide rotational stability for concave prosthetic component 304 and allow bony ingrowth.

As shown in FIG. 12C, an inner surface 326 of concave prosthetic component 304 includes concave ellipsoidal surface 310 and a cylindrical surface 328. The distance D2 from cylindrical surface 328 to the apex of inner surface 326 may be approximately 7 mm. The distance D3 across a major axis 330 of ellipsoidal surface 310 may be approximately 21 mm. As shown in FIG. 12D, a distance D4 across a minor axis 332 of ellipsoidal surface 310 may be approximately 14 mm. The three principal semi-axes of ellipsoidal surface 310 are preferably 10.5 mm, 7 mm, and 7 mm, consistent with the distances D2, D3, and D4.

Elbow arthroplasty systems 10, 100, 200, 500, and 600 described herein may have similar dimensions as noted herein with respect to elbow arthroplasty system 300.

Figure 13:
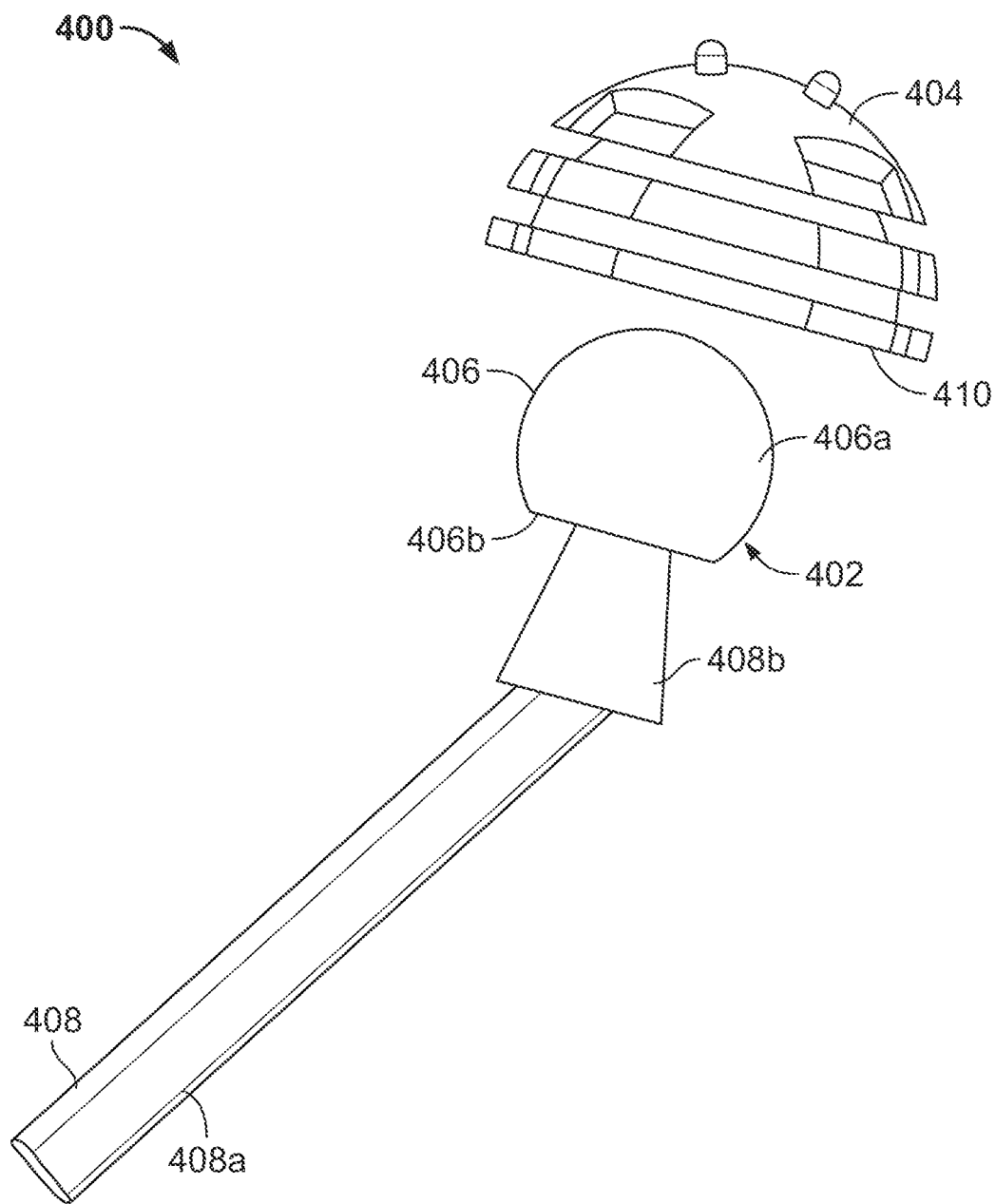
FIG. 13 is a perspective view of an alternative embodiment of elbow arthroplasty system having spherical prosthetic components.

Another alternative embodiment of elbow arthroplasty system is generally identified as 400 in FIG. 13. Elbow arthroplasty system 400 includes a convex prosthetic component 402 and a concave prosthetic component, or socket, 404. Convex prosthetic component 402 includes a ball 406 that is a portion of a sphere and is joined to an end of a stem 408. Ball 406 is a truncated sphere with a spherical outer surface 406a and a flat surface 406b that is joined to stem 408. Stem 408 includes a first section 408a and a second section 408b. First section 408a is an elongate rod with a cross-section that is generally rectangular with rounded ends. Second section 408b is shaped as a conical frustum tapering in size from first section 408a toward ball 406. First section 408a of stem 408 may be surgically attached to a proximal portion of an ulna in a similar manner as shown in FIGS. 1A-1B for stem 18. Alternatively, stem 408 may be surgically attached to a proximal portion of a radius, proximal portions of a radius and an ulna, or a distal portion of a humerus. Second section 408b may abut a portion of an ulna, radius, or humerus when first section 408a is inserted in a hole in the ulna, radius, or humerus to position ball 406 in a desired location with respect to the ulna, radius, or humerus. For example, second section 408b may abut the ulna, radius, or humerus to position ball 406 with respect to an ulna so that central axis 414 (FIGS. 14A-B) of ball 406 is generally aligned with a radial center of a trochlear notch of the ulna. In this manner, second section 408b acts as a spacer or positional guide that spaces ball 406 a desired distance from the ulna.

Concave prosthetic component 404 has a concave spherical surface 410 that defines a cavity 412 (FIG. 15C) for receiving a portion of ball 406. Concave prosthetic component 404 may be surgically attached to a distal portion of a humerus in a similar manner as shown in FIGS. 2A-2B for concave prosthetic component 24. Alternatively, concave prosthetic component 404 may be surgically attached to a proximal portion of an ulna, a proximal portion of a radius, or proximal portions of a radius and an ulna. Convex and concave prosthetic components 402 and 404 mate and articulate with each other in a similar manner as described above for elbow arthroplasty systems 10, 100, and 200 such that elbow arthroplasty system 400 mimics the natural articulation of an elbow when in use.

As shown in FIG. 14A, there is an angle X1 between a central axis 414 of spherical ball 406 and first section 408a of stem 408. Angle X1 may be between 56 to 66 degrees, is more preferably between 59 to 63 degrees, and is most preferably approximately 61 degrees. The diameter d2 of second section 408b where it is joined to first section 408a may be approximately 8 mm. The diameter of ball 406 may be approximately 12 mm. The width and thickness of first section 408a may be substantially the same as described above for first section 308a.

As shown in FIG. 14B, the length of second section 408b from first section 408a to ball 406 may be substantially the same as described above for second section 308b (i.e., 8 mm). The distance D5 from second section 408b to the central axis 414 may be approximately 4 mm. The combination of the length of second section 408 and D5, which is preferably approximately 12 mm, represents the distance from the bone to the central axis 414 of ball 406 when first section 408a of stem 408 is inserted into the bone.

As shown in FIG. 14C, there is an angle Y1 between first section 408a of stem 408 and a central axis of the second section 408b of stem 408. Angle Y1 may be between 141 to 151 degrees, is more preferably between 144 to 148 degrees, and is most preferably approximately 146 degrees. The length of first section 408a may be substantially the same as described above for first section 308a. The outer surface of second section 408b may taper at an angle that is substantially the same as described above for second section 308b.

The angles X1 and Y1 and other dimensions referenced above preferably allow first section 408a to be securely attached to an ulna, a radius, an ulna and a radius, or a humerus, and ball 406 to be positioned so that articulation of elbow arthroplasty system 400 is similar to a natural elbow.

Figure 15A:
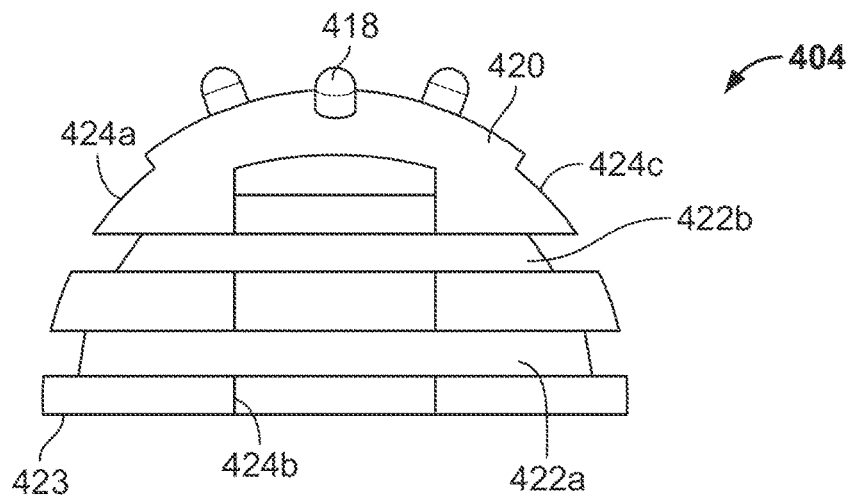
FIG. 15A is a side elevational view of a concave prosthetic component of the elbow arthroplasty system shown in FIG. 13.
Figure 15B:
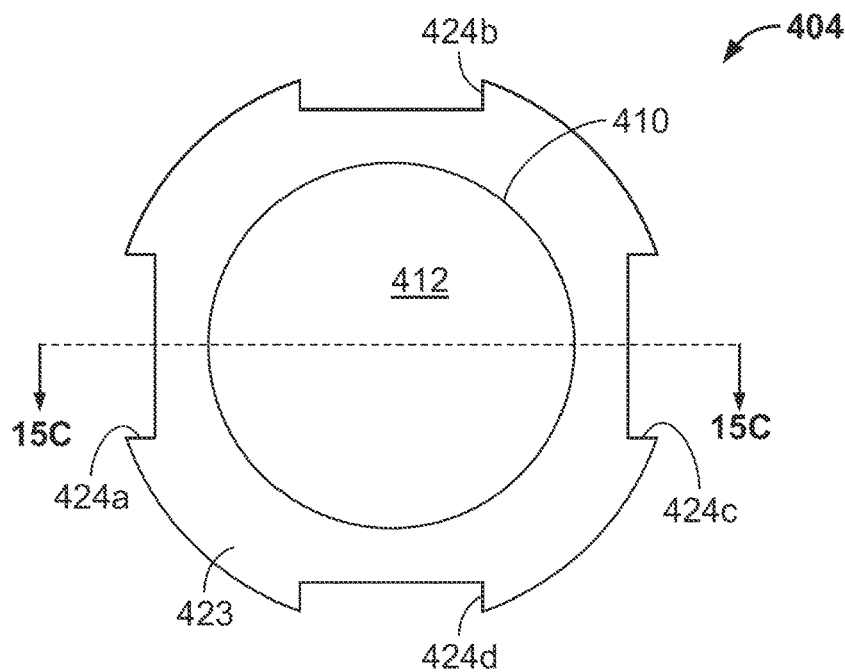
FIG. 15B is a top plan view of the concave prosthetic component shown in FIG. 15A.
Figure 15C:
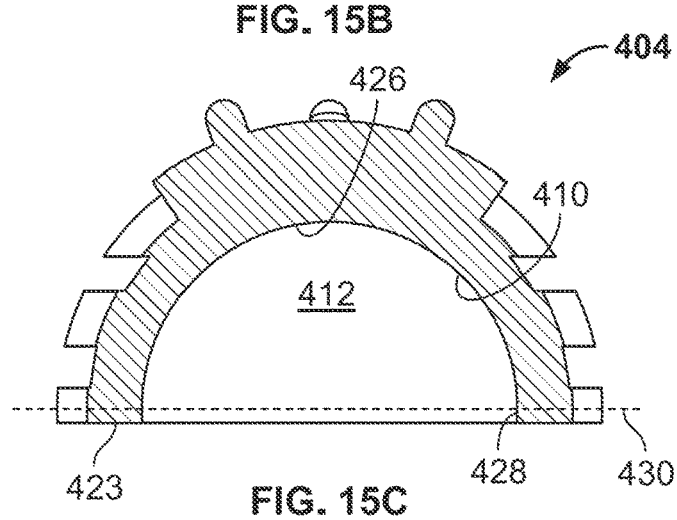
FIG. 15C is a cross-sectional view taken through the line 15C-15C of FIG. 15B.

Referring to FIGS. 15A-C, concave prosthetic component 404 is generally a truncated sphere with a hollow center that forms cavity 412. A plurality of protrusions (one of which is identified as 418) extend outward from an apex of an outer surface 420. Further, two circumferential grooves 422a-b extend around outer surface 420. Grooves 422a-b extend around outer surface 420 in planes oriented with a truncated surface 423 of concave prosthetic component 404. Notches 424*a-d* are further formed in outer surface 420, as shown in FIG. 15B. As shown in FIGS. 15A-B, notches 424*a-d* extend upward from truncated surface 423 approximately two-thirds of the way up toward the apex of outer surface 420. Notches 424*a-d* are spaced apart from each other approximately 90 degrees around the circumference of outer surface 420. Protrusions 418, grooves 422*a-b*, and notches 424*a-d* preferably aid in surgically attaching concave prosthetic component 404 to an ulna, radius, or humerus. For example, protrusions 418, grooves 422*a-b*, and notches 424*a-d* provide rotational stability for concave prosthetic component 404 and allow bony ingrowth.

As shown in FIG. 15C, an inner surface 426 of concave prosthetic component 404 includes concave spherical surface 410 and a cylindrical surface 428. Spherical surface 410 has a central axis 430. The radius of spherical surface 410 may be approximately 7 mm.

Elbow arthroplasty systems 10, 100, 200, 500, and 600 described herein may have similar dimensions as noted herein with respect to elbow arthroplasty system 400.

FIGS. 16A-B show an elbow arthroplasty system 500 that includes a convex prosthetic component 502 and a concave prosthetic component 504. Convex prosthetic component 502 includes a ball 506 that is joined to a base 508. Ball 506 may be ellipsoidal, spheroidal, or spherical as described and shown above with respect to elbow arthroplasty systems 10, 100, 200, 300, and 400. Base 508 includes two protrusions 510, 512 that extend outward from base 508. Protrusions 510, 512 are shown inserted into holes formed in ulna 514. Base 508 is surgically fitted to and affixed to the proximal ulna 514 preferably using bone cement, screws, pins, and/or press-fit fixation. Base 508 may be cemented to ulna 514 or un-cemented with porous or bone ingrowth. Ball 506 is preferably positioned with respect to ulna 514 as described above in connection with elbow arthroplasty system 10.

Concave prosthetic component, or socket, 504 includes a concave surface 516 that may be ellipsoidal, spheroidal, or spherical as described and shown above with respect to elbow arthroplasty systems 10, 100, 200, 300, and 400. Concave surface 516 is configured to receive ball 506 so that ball 506 articulates with concave surface 516 in a manner that is similar to natural humeroulnar articulation as described above with respect to elbow arthroplasty system 10. Concave prosthetic component 504 includes a base 518 having two protrusions 520, 522 that extend outward from base 518. Protrusions 520, 522 are shown inserted into holes formed in humerus 524. Base 518 is surgically fitted to and affixed to the distal humerus 524 preferably using bone cement, screws, pins, and/or press-fit fixation. Base 518 may be cemented to humerus 524 or un-cemented with porous or bone ingrowth. Concave surface 516 is preferably positioned with respect to humerus 524 as described above in connection with elbow arthroplasty system 10. Elbow arthroplasty system 500 may be configured to replace the humeroulnar joint, the humeroradial joint, or both the humeroulnar and humeroradial joints.

FIGS. 17A-B show an elbow arthroplasty system 600 that includes a concave prosthetic component 602 and a convex prosthetic component 604. Elbow arthroplasty system 600 is substantially similar to elbow arthroplasty system 500 except that concave prosthetic component 602 is joined to a proximal portion of an ulna 606 and convex prosthetic component 604 is joined to a distal portion of a humerus 608.

Elbow arthroplasty systems 10, 100, 200, 300, 400, 500, and 600 are used in a similar manner. Accordingly, only use of elbow arthroplasty system 10 is described in detail herein.

Convex prosthetic component 12 is joined to ulna 14 by forming a cavity in ulna 14 for receiving first section 18*a* of stem 18 (FIGS. 1A-B). First section 18*a* is inserted into the cavity and ball 16 is positioned with respect to ulna 14 so that major axis 20 of ball 16 is generally aligned with a radial center of a trochlear notch 22 of ulna 14. A positional guide or spacer on stem 18 (e.g. second sections 308*b* or 408*b*) may space ball 16 the desired distance. Convex prosthetic component 12 is surgically attached to ulna 14 using at least one of the following: bone cement, a screw or screws, a pin or pins, and press-fit fixation. Convex prosthetic component 12 may be cemented to ulna 14 or un-cemented with porous or bone ingrowth. Alternatively, convex prosthetic component 12 may be surgically attached to a humerus (e.g., similar to elbow arthroplasty system 200), a radius, or a radius and an ulna.

Humerus 26 is prepared for receiving concave prosthetic component 24 by, for example, cutting or grinding away a portion of humerus 26 (FIGS. 2A-B). Concave prosthetic component 24 is positioned with respect to humerus 26 so that major axis 20 of ball 16 (when ball 16 is received by concave prosthetic component 24) is generally aligned with a center of rotation of a trochlea of humerus 26. Concave prosthetic component 24 is surgically attached to humerus 26 using at least one of the following: bone cement, a screw or screws, a pin or pins, and press-fit fixation. Concave prosthetic component 24 may be cemented to ulna 14 or un-cemented with porous or bone ingrowth. Alternatively, concave prosthetic component 24 may be surgically attached to an ulna (e.g., similar to elbow arthroplasty system 200), a radius, or a radius and an ulna.

Ball 16 is aligned with concave prosthetic component 24 in the manner shown in FIGS. 3A-3D and positioned within cavity 30. Ball 16 is then able to articulate with respect to concave prosthetic component 24 in a manner that is similar to natural humeroulnar articulation.

While this specification describes a number of embodiments, aspects of each embodiment may be applied to other embodiments. Thus, this specification contemplates that the various features of the embodiments may be combined with one another.

We claim:

1. An elbow arthroplasty method comprising:
providing a convex prosthetic component comprising a ball with a surface coupled to a stem, wherein the ball is an ellipsoid or a portion of an ellipsoid, wherein the ball comprises an ellipsoidal outer surface extending continuously outward from a peripheral edge of the surface coupled to the stem;
surgically fitting and affixing the stem of the convex prosthetic component to at least one member of one of the following groups: (i) a humerus, or (ii) a radius, an ulna, or both of the radius and the ulna, in a manner in which the ball is not rotatable with respect to the at least one member of the following groups: (i) the humerus, or (ii) the radius, the ulna, or both of the radius and the ulna to which the convex prosthetic component is affixed;
coupling a socket to at least one member of the other of the following groups: (i) the humerus, or (ii) the radius, the ulna, or both of the radius and the ulna, the socket having a concave ellipsoidal surface defining a cavity and an opening through which the cavity is accessible; and
positioning at least a portion of the ball within the cavity defined by the socket, and wherein when the ball is positioned within the cavity, the ball is rotatable with respect to the socket about a first axis allowing flexion rotation and extension rotation of the ulna relative to the humerus, a second axis allowing abduction rotation and adduction rotation of the ulna relative to the humerus, and a third axis allowing internal rotation and external rotation of the ulna relative to the humerus.

2. The method of claim 1, wherein the convex prosthetic component is surgically fitted and affixed to at least one of a proximal portion of the radius or a proximal portion of the ulna, and wherein the socket is coupled to a distal portion of the humerus.

3. The method of claim 2, wherein the convex prosthetic component is surgically fitted and affixed to both of the proximal portion of the radius and the proximal portion of the ulna.

4. The method of claim 1, wherein the convex prosthetic component is surgically fitted and affixed to a distal portion of the humerus, and wherein the socket is coupled to at least one of a proximal portion of the radius or a proximal portion of the ulna.

5. The method of claim 4, wherein the socket is coupled to both of the proximal portion of the radius and the proximal portion of the ulna.

6. The method of claim 1, wherein the ball is positioned with respect to the ulna so that a major axis of the ellipsoid is generally aligned with a radial center of a trochlear notch of the ulna.

7. The method of claim 6, wherein the socket is positioned with respect to the humerus so that the major axis of the ellipsoid is generally aligned with a center of rotation of the humerus trochlea when the ball is received in the cavity and articulates with the socket.

8. The method of claim 1, wherein the ball and the socket are positioned with respect to the humerus and the ulna so that as the ball articulates with the socket the ulna rotates with respect to the humerus in a manner that is similar to natural humeroulnar articulation.

9. The method of claim 1, wherein the ball and the socket replace a humeroradial joint and a humeroulnar joint.

10. The method of claim 1, wherein the ball and the socket are each formed from at least one of the following materials: a metal, a ceramic, or a polymer.

11. The method of claim 1, wherein the convex prosthetic component and the socket are each surgically fitted and affixed to at least one of the humerus, the radius, or the ulna using at least one of the following: bone cement, a screw, a pin, or press-fit fixation.

12. An elbow arthroplasty system comprising:
a convex prosthetic component comprising a ball, wherein the ball is an ellipsoid or a portion of an ellipsoid, the convex prosthetic component configured to be surgically fitted and affixed to at least one member of one of the following groups: (i) a humerus, or (ii) a radius, an ulna, or both of the radius and the ulna, in a manner in which the ball is not rotatable with respect to the at least one member of the following groups: (i) the humerus, or (ii) the radius, the ulna, or both of the radius and the ulna to which the convex prosthetic component is affixed, wherein the ball comprises a surface coupled to a stem, and wherein the ball comprises an ellipsoidal outer surface extending continuously outward from a peripheral edge of the surface coupled to the stem; and
a socket configured for coupling to at least one member of the other of the following groups: (i) the humerus, or (ii) the radius, the ulna, or both of the radius and the ulna, wherein the socket comprises a concave ellipsoidal surface defining a cavity that is configured to receive at least a portion of the ball, and
wherein when the convex prosthetic component is affixed to the at least one member of the following groups: (i) the humerus, or (ii) the radius, the ulna, or both of the radius and the ulna and the socket is coupled to the at least one member of the other of the following groups: (i) the humerus, or (ii) the radius, the ulna, or both of the radius and the ulna, the ball is rotatable with respect to the socket about a first axis allowing flexion rotation and extension rotation of the ulna relative to the humerus, a second axis allowing abduction rotation and adduction rotation of the ulna relative to the humerus, and a third axis allowing internal rotation and external rotation of the ulna relative to the humerus, and
wherein the ball is insertable in the cavity when a longitudinal axis of the ulna is generally aligned with a longitudinal axis of the humerus.

13. The system of claim 12, wherein when the convex prosthetic component is affixed to the at least one member of the following groups: (i) the humerus, or (ii) the radius, the ulna, or both of the radius and the ulna and the socket is coupled to the at least one member of the other of the following groups: (i) the humerus, or (ii) the radius, the ulna, or both of the radius and the ulna, the ball is movable with respect to the socket in a manner that allows anterior translation and posterior translation of the ulna relative to the humerus, superior translation and inferior translation of the ulna relative to the humerus, and medial translation and lateral translation of the ulna relative to the humerus.

14. The system of claim 12, wherein the ball and the socket are each formed from at least one of the following materials: a metal, a ceramic, or a polymer.

15. The system of claim 12, wherein the stem and the socket are each configured to be surgically fitted and affixed to at least one of a humerus, a radius, or an ulna using at least one of the following: bone cement, a screw, a pin, or press-fit fixation.

16. The system of claim 12, wherein the stem comprises a spacer that is configured to abut a bone when a portion of the stem is inserted in the bone.

17. The system of claim 12, wherein the convex prosthetic component is configured to be surgically fitted and affixed to at least one of a proximal portion of the radius or a proximal portion of the ulna, and wherein the socket is configured for coupling to a distal portion of the humerus.

18. The system of claim 17, wherein the convex prosthetic component is configured to be surgically fitted and affixed to both of the proximal portion of the radius and the proximal portion of the ulna.

19. The system of claim 12, wherein the convex prosthetic component is configured to be surgically fitted and affixed to a distal portion of the humerus, and wherein the socket is configured for coupling to at least one of a proximal portion of the radius or a proximal portion of the ulna.

20. The system of claim 19, wherein the socket is configured for coupling to both of the proximal portion of the radius and the proximal portion of the ulna.

21. The system of claim 12, wherein the socket comprises at least one protrusion that is configured for insertion into at least one of the humerus, the radius, the ulna, or both of the radius and the ulna.

22. An elbow arthroplasty system comprising:
a convex prosthetic component comprising a ball, the convex prosthetic component configured to be surgically fitted and affixed to both of a proximal portion of a radius and a proximal portion of an ulna in a manner in which the ball is not rotatable with respect to both of the radius and the ulna, wherein the ball comprises a surface coupled to a stem, and wherein the ball comprises a spherical, spheroidal, or ellipsoidal outer surface extending continuously outward from a peripheral edge of the surface coupled to the stem; and a socket configured for coupling to a distal portion of a humerus, wherein the socket defines a cavity that is configured to receive at least a portion of the ball, and wherein when the convex prosthetic component is affixed to both of the radius and the ulna and the socket is coupled to the humerus, the ball is rotatable with respect to the socket about a first axis allowing flexion rotation and extension rotation of the ulna relative to the humerus, a second axis allowing abduction rotation and adduction rotation of the ulna relative to the humerus, and a third axis allowing internal rotation and external rotation of the ulna relative to the humerus, and wherein the ball is insertable in the cavity when a longitudinal axis of the ulna is generally aligned with a longitudinal axis of the humerus.

23. The system of claim 22, wherein the ball is a sphere or a portion of a sphere, and wherein the socket comprises a concave spherical surface defining the cavity.

24. The system of claim 22, wherein the ball is an ellipsoid or a portion of an ellipsoid, and wherein the socket comprises a concave ellipsoidal surface defining the cavity.

25. An elbow arthroplasty system comprising:

a convex prosthetic component comprising a ball, the convex prosthetic component configured to be surgically fitted and affixed to a distal portion of a humerus in a manner in which the ball is not rotatable with respect to the humerus, wherein the ball comprises a surface coupled to a stem, and wherein the ball comprises a spherical, spheroidal, or ellipsoidal outer surface extending continuously outward from a peripheral edge of the surface coupled to the stem; and a socket configured for coupling to both of a proximal portion of a radius and a proximal portion of an ulna, wherein the socket defines a cavity that is configured to receive at least a portion of the ball, and wherein when the convex prosthetic component is affixed to the humerus, and the socket is coupled to both of the radius and the ulna, the ball is rotatable with respect to the socket about a first axis allowing flexion rotation and extension rotation of the ulna relative to the humerus, a second axis allowing abduction rotation and adduction rotation of the ulna relative to the humerus, and a third axis allowing internal rotation and external rotation of the ulna relative to the humerus, and wherein the ball is insertable in the cavity when a longitudinal axis of the ulna is generally aligned with a longitudinal axis of the humerus.

26. An elbow arthroplasty method comprising:

providing a convex prosthetic component comprising a ball with a surface coupled to a stem, wherein the ball comprises a spherical, spheroidal, or ellipsoidal outer surface extending continuously outward from a peripheral edge of the surface coupled to the stem;

surgically fitting and affixing the stem of the convex prosthetic component to both of a proximal portion of a radius and a proximal portion of an ulna in a manner in which the ball is not rotatable with respect to both of the radius and the ulna;

coupling a socket to a distal portion of a humerus, the socket having a concave surface defining a cavity and an opening through which the cavity is accessible; and positioning at least a portion of the ball within the cavity defined by the socket, and wherein when the ball is positioned within the cavity, the ball is rotatable with respect to the socket about a first axis allowing flexion rotation and extension rotation of the ulna relative to the humerus, a second axis allowing abduction rotation and adduction rotation of the ulna relative to the humerus, and a third axis allowing internal rotation and external rotation of the ulna relative to the humerus.

27. The method of claim 26, wherein the ball is a sphere or a portion of a sphere, and wherein the socket comprises a concave spherical surface defining the cavity.

28. The method of claim 26, wherein the ball is an ellipsoid or a portion of an ellipsoid, and wherein the socket comprises a concave ellipsoidal surface defining the cavity.

29. An elbow arthroplasty method comprising:

providing a convex prosthetic component comprising a ball with a surface coupled to a stem, wherein the ball comprises a spherical, spheroidal, or ellipsoidal outer surface extending continuously outward from a peripheral edge of the surface coupled to the stem;

surgically fitting and affixing the stem of the convex prosthetic component to a distal portion of a humerus in a manner in which the ball is not rotatable with respect to the humerus;

coupling a socket to both of a proximal portion of a radius and a proximal portion of an ulna, the socket having a concave surface defining a cavity and an opening through which the cavity is accessible; and positioning at least a portion of the ball within the cavity defined by the socket, and wherein when the ball is positioned within the cavity, the ball is rotatable with respect to the socket about a first axis allowing flexion rotation and extension rotation of the ulna relative to the humerus, a second axis allowing abduction rotation and adduction rotation of the ulna relative to the humerus, and a third axis allowing internal rotation and external rotation of the ulna relative to the humerus.

\* \* \* \* \*